United States Patent
DiMaio et al.

(10) Patent No.: US 12,213,757 B2
(45) Date of Patent: *Feb. 4, 2025

(54) MASTER/SLAVE REGISTRATION AND CONTROL FOR TELEOPERATION

(71) Applicant: INTUITIVE SURGICAL OPERATIONS, INC., Sunnyvale, CA (US)

(72) Inventors: Simon P. DiMaio, San Carlos, CA (US); Gerard J. Labonville, San Jose, CA (US); Kollin M. Tierling, Los Altos Hills, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/513,322

(22) Filed: Nov. 17, 2023

(65) Prior Publication Data

US 2024/0156554 A1    May 16, 2024

Related U.S. Application Data

(63) Continuation of application No. 17/990,318, filed on Nov. 18, 2022, now Pat. No. 11,857,280, which is a
(Continued)

(51) Int. Cl.
*H04N 23/00* (2023.01)
*A61B 1/00* (2006.01)
(Continued)

(52) U.S. Cl.
CPC .......... *A61B 34/35* (2016.02); *A61B 1/00149* (2013.01); *A61B 34/37* (2016.02);
(Continued)

(58) Field of Classification Search
CPC ..... A61B 34/35; A61B 1/00149; A61B 34/37; A61B 17/02; A61B 17/068;
(Continued)

(56) References Cited

U.S. PATENT DOCUMENTS

| 4,574,199 A | * | 3/1986 | Pryor | G01B 11/007 33/503 |
| 5,243,665 A | * | 9/1993 | Maney | H01L 21/67259 382/280 |

(Continued)

FOREIGN PATENT DOCUMENTS

| CN | 105773629 A | 7/2016 |
| WO | WO-2013023130 A1 | 2/2013 |

(Continued)

OTHER PUBLICATIONS

Extended European Search Report for Application No. EP18877895.5 mailed on Nov. 25, 2020, 9 pages.

(Continued)

*Primary Examiner* — Frank F Huang
(74) *Attorney, Agent, or Firm* — Haynes & Boone, LLP.

(57) ABSTRACT

A teleoperated system comprises a display, a master input device, and a control system. The control system is configured to determine an orientation of an end effector reference frame relative to a field of view reference frame, determine an orientation of a master input device reference frame relative to a display reference frame, establish an alignment relationship between the master input device reference frame and the display reference frame, and command, based on the alignment relationship, a change in a pose of the end effector in response to a change in a pose of the master input device. The alignment relationship is independent of a position relationship between the master input device reference frame and the display reference frame. In one aspect, (Continued)

the teleoperated system is a telemedical system such as a telesurgical system.

20 Claims, 13 Drawing Sheets

Related U.S. Application Data continuation of application No. 16/763,556, filed as application No. PCT/US2018/060612 on Nov. 13, 2018, now Pat. No. 11,534,252.

(60) Provisional application No. 62/587,175, filed on Nov. 16, 2017.

(51) Int. Cl.
| | | |
|---|---|---|
| *A61B 34/35* | (2016.01) | |
| *A61B 34/37* | (2016.01) | |
| *G05B 19/4155* | (2006.01) | |
| *G16H 30/40* | (2018.01) | |
| *G16H 40/67* | (2018.01) | |
| *H04N 23/54* | (2023.01) | |
| *A61B 17/02* | (2006.01) | |
| *A61B 17/068* | (2006.01) | |
| *A61B 17/128* | (2006.01) | |
| *A61B 17/29* | (2006.01) | |
| *A61B 17/32* | (2006.01) | |
| *A61B 17/3201* | (2006.01) | |
| *A61B 18/00* | (2006.01) | |
| *A61B 34/00* | (2016.01) | |
| *A61B 90/00* | (2016.01) | |
| *H04N 23/50* | (2023.01) | |

(52) U.S. Cl.
CPC ......... *G05B 19/4155* (2013.01); *G16H 30/40* (2018.01); *G16H 40/67* (2018.01); *H04N 23/54* (2023.01); *A61B 17/02* (2013.01); *A61B 17/068* (2013.01); *A61B 17/1285* (2013.01); *A61B 17/29* (2013.01); *A61B 17/320068* (2013.01); *A61B 17/3201* (2013.01); *A61B 2018/00595* (2013.01); *A61B 34/71* (2016.02); *A61B 2034/741* (2016.02); *A61B 2034/742* (2016.02); *A61B 2090/374* (2016.02); *A61B 2090/376* (2016.02); *A61B 2090/3762* (2016.02); *A61B 2090/378* (2016.02); *A61B 2217/005* (2013.01); *A61B 2217/007* (2013.01); *G05B 2219/40174* (2013.01); *H04N 23/555* (2023.01)

(58) Field of Classification Search
CPC ............... A61B 17/1285; A61B 17/29; A61B 17/320068; A61B 17/3201; A61B 34/71; A61B 2018/00595; A61B 2034/741; A61B 2034/742; A61B 2090/374; A61B 2090/376; A61B 2090/3762; A61B 2090/378; A61B 2217/005; A61B 2217/007; A61B 90/37; A61B 2090/364; A61B 90/36; A61B 34/74; G05B 19/4155; G05B 2219/40174; G16H 30/40; G16H 40/67; G16H 80/00; H04N 5/2253; H04N 2005/2255
See application file for complete search history.

(56) References Cited

U.S. PATENT DOCUMENTS

| | | | | |
|---|---|---|---|---|
| 5,920,394 A | * | 7/1999 | Gelbart | G01S 17/66 |
| | | | | 356/615 |
| 6,044,308 A | | 3/2000 | Huissoon | |
| 6,364,888 B1 | | 4/2002 | Niemeyer et al. | |
| 6,926,709 B2 | | 8/2005 | Bieger et al. | |
| 7,010,390 B2 | | 3/2006 | Graf et al. | |
| 8,108,072 B2 | | 1/2012 | Zhao et al. | |
| 8,506,555 B2 | | 8/2013 | Ruiz Morales | |
| 8,535,336 B2 | * | 9/2013 | Trovato | A61B 17/3421 |
| | | | | 606/130 |
| 8,818,560 B2 | | 8/2014 | Kishi | |
| 9,259,289 B2 | | 2/2016 | Zhao et al. | |
| 9,827,057 B2 | | 11/2017 | Zhao et al. | |
| 10,646,156 B1 | * | 5/2020 | Schnorr | G06N 3/0454 |
| 10,883,708 B2 | * | 1/2021 | Chien | F21V 5/04 |
| 11,534,252 B2 | | 12/2022 | DiMaio et al. | |
| 11,857,280 B2 | | 1/2024 | DiMaio et al. | |
| 2005/0107920 A1 | | 5/2005 | Ban et al. | |
| 2006/0258938 A1 | | 11/2006 | Hoffman et al. | |
| 2008/0262312 A1 | * | 10/2008 | Carroll | A61B 1/07 |
| | | | | 600/160 |
| 2009/0046146 A1 | * | 2/2009 | Hoyt | A61B 1/0004 |
| | | | | 345/169 |
| 2009/0088634 A1 | * | 4/2009 | Zhao | B25J 9/1656 |
| | | | | 600/425 |
| 2009/0305210 A1 | * | 12/2009 | Guru | B25J 9/1671 |
| | | | | 434/262 |
| 2010/0125282 A1 | | 5/2010 | Machek et al. | |
| 2010/0204714 A1 | | 8/2010 | Shoham | |
| 2011/0270084 A1 | | 11/2011 | Choi et al. | |
| 2011/0320039 A1 | | 12/2011 | Hsu et al. | |
| 2014/0100694 A1 | | 4/2014 | Rueckl et al. | |
| 2014/0171964 A1 | * | 6/2014 | Yang | A61B 34/37 |
| | | | | 606/130 |
| 2014/0207541 A1 | * | 7/2014 | Nerayoff | G06Q 50/30 |
| | | | | 382/104 |
| 2015/0173846 A1 | * | 6/2015 | Schneider | G02B 27/017 |
| | | | | 600/424 |
| 2016/0023355 A1 | | 1/2016 | Komatsu et al. | |
| 2016/0030117 A1 | | 2/2016 | Mewes | |
| 2016/0346930 A1 | | 12/2016 | Hares | |
| 2017/0112582 A1 | | 4/2017 | Itkowitz et al. | |
| 2019/0293935 A1 | * | 9/2019 | Schneider | A61B 5/748 |
| 2020/0138518 A1 | * | 5/2020 | Lang | A61B 5/05 |
| 2021/0192759 A1 | * | 6/2021 | Lang | G06T 7/33 |
| 2021/0369365 A1 | | 12/2021 | Goswami et al. | |
| 2022/0241030 A1 | * | 8/2022 | Yoon | A61B 90/50 |
| 2023/0131431 A1 | | 4/2023 | DiMaio et al. | |

FOREIGN PATENT DOCUMENTS

| | | |
|---|---|---|
| WO | WO-2015142802 A1 | 9/2015 |
| WO | WO-2016069655 A1 | 5/2016 |
| WO | WO-2016137527 A1 | 9/2016 |
| WO | WO-2016201207 A1 | 12/2016 |
| WO | WO-2019139949 A1 | 7/2019 |

OTHER PUBLICATIONS

International Preliminary Report on Patentability for Application No. PCT/US2018/060612, mailed on May 28, 2020, 8 pages (ISRG06150/PCT).
International Search Report and Written Opinion for Application No. PCT/US2018/060612, mailed on May 3, 2019, 13 pages (ISRG06150/PCT).
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

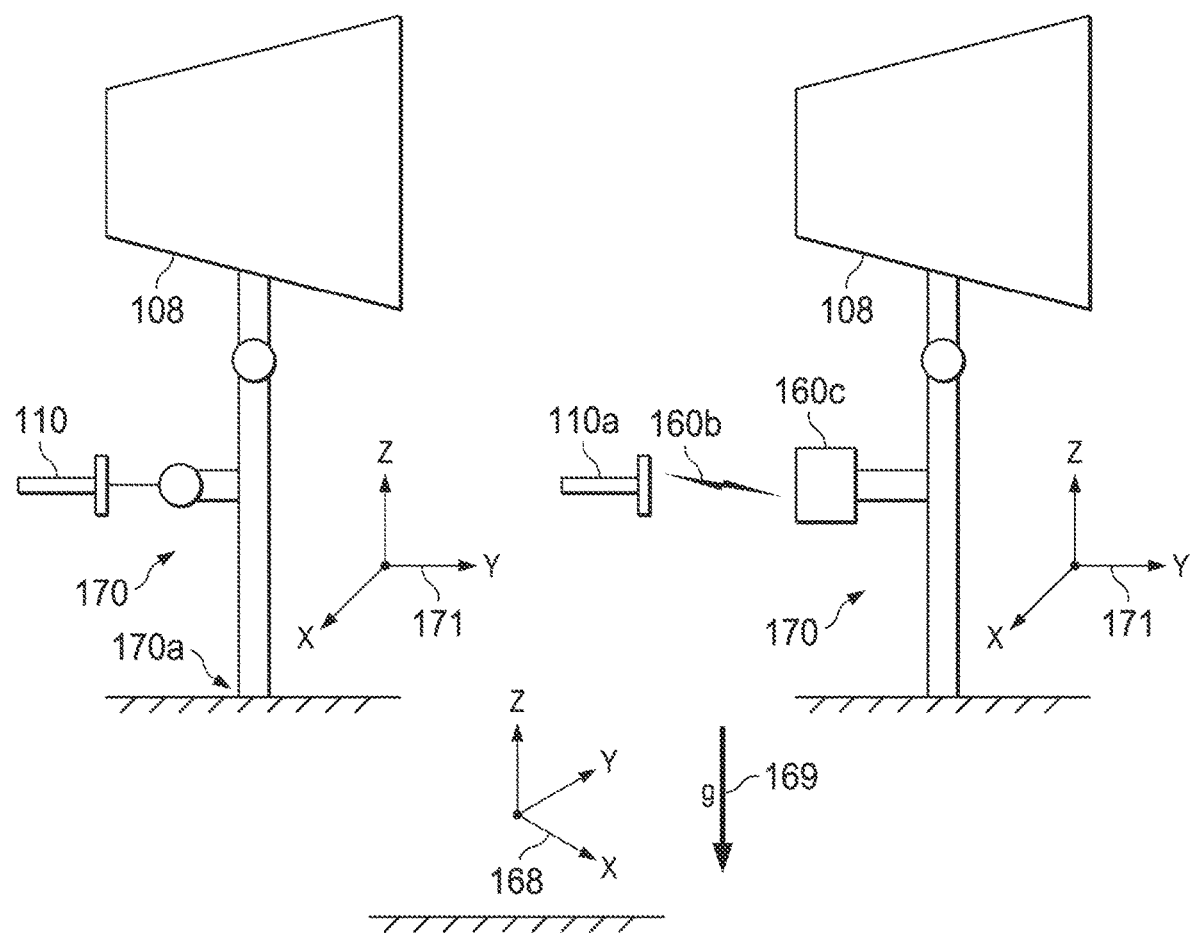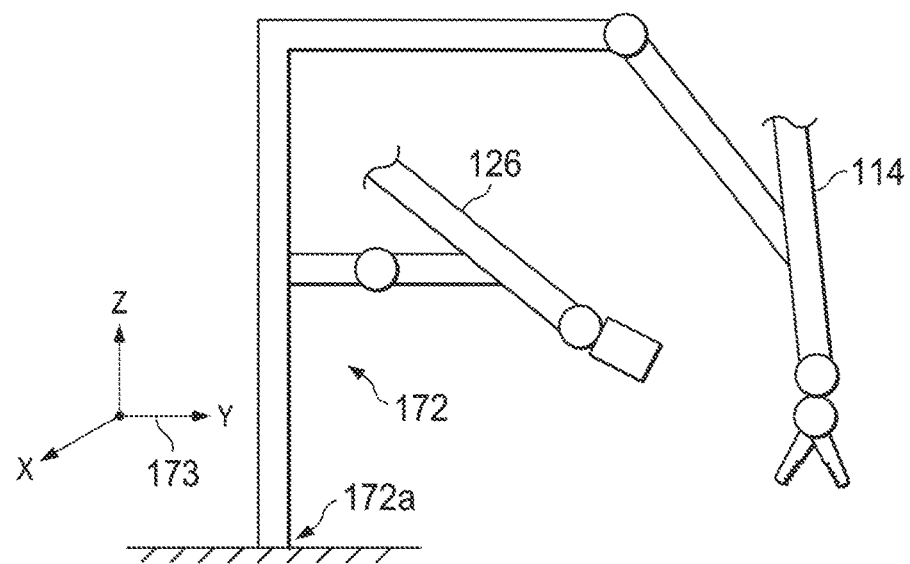
Fig. 5C

MASTER/SLAVE REGISTRATION AND CONTROL FOR TELEOPERATION

CROSS-REFERENCE TO RELATED APPLICATIONS

This patent application is a continuation of U.S. patent application Ser. No. 17/990,318, filed Nov. 18, 2022, which is a continuation of U.S. patent application Ser. No. 16/763,556, filed May 13, 2020, which is the U.S. national phase of International Application No. PCT/US2018/060612, filed Nov. 13, 2018, which designated the U.S. and claims priority to and the benefit of the filing date of U.S. Provisional Application 62/587,175, filed Nov. 16, 2017, all of which are incorporated by reference in their entirety.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Technical Field

The present disclosure is generally related to teleoperated systems, and more specifically to spatial registration and control in teleoperated systems.

Background

Examples of teleoperated systems include industrial and recreational systems. Examples of teleoperated systems also include medical teleoperated systems used in procedures for diagnosis, non-surgical treatment, surgical treatment, etc. A teleoperated, robotic medical system usable for telesurgery or other telemedical procedures can include one or more remotely controllable robotic manipulators. In some implementations, the remotely controllable robotic manipulators may also be configured to be manually articulated or moved.

A minimally invasive, robotic, telesurgical system is a specific example of a teleoperated system that enables surgeons to perform surgical procedures on a patient by using some form of remote control of instrument movement, instead of directly holding and moving the instruments by hand. Surgical systems that incorporate robotic technology under at least partial computer control to perform minimally invasive surgery have extended the benefits of minimally invasive surgery. For example, certain surgical procedures that would be difficult or impossible with manually operated minimally invasive surgical tools may be made possible with the use of such surgical systems. An example of such surgical systems is the da Vinci® Surgical Systems commercialized by Intuitive Surgical, Inc. of Sunnyvale, California, U.S.A.

To establish the required control relationship between a master input device (also called "master control device" or "master device") and the corresponding tool for a conventional teleoperated system, the kinematic poses of the master control device and of the tool are determined in three-dimensional (3D) space. In the da Vinci Xi® Surgical Systems commercialized by Intuitive Surgical, the patient-side unit offers a known and defined kinematic structure that allows the tool's pose to be determined. Likewise, the surgeon's console offers a known and defined kinematic structure on which the master input device pose can be determined. New teleoperated system architectures may lack a single mechanical base common to the tools that can be used in determining the kinematic relationships among the tools. Similarly, new teleoperated system architectures may lack a mechanical base common to the master input devices that can be used to determine the kinematic relationships among the master input devices, or between the master input device(s) and other equipment such as a display. Thus, there is a need to for improved spatial registration and control in teleoperated systems.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its purpose is to present some aspects and embodiments in a general form as a prelude to the more detailed description below.

In an aspect, a teleoperated system includes an imaging device, an end effector, a display, a master input device, and a computer control system. The imaging device has a field of view. Reference frames are defined for the field of view, the end effector, the display, and the master input device. The control system determines complete orientation information for the reference frames, but less than full position information for the reference frames. Complete orientation information is also called full orientation information, and full position information is also called complete position information. In one aspect, the control system does not determine any position information about the reference frames. In another aspect, the control system determines partial position information about the reference frames. The control system establishes a master/slave control relationship between the master device and the end effector by using the complete orientation information of the reference frames, but less than complete position information (partial position information or no position information) for the reference frames.

In various aspects, the teleoperated system includes various ways to determine the complete orientation information of the reference frames, and also to determine the less than complete position information of the reference frames as applicable. These ways include the use of one or more of a temporary localized mechanical relationship between a pair of teleoperated system units, a fixed-sensor locator system, a fixed-feature locator system, a simultaneous localization and mapping system, a machine vision system that uses images from the imaging device, an optical fiber shape sensor, an accelerometer, a magnetometer, a gyroscope, a vibration detector, and a vibration injector.

In an aspect, a teleoperated system comprises a display, a master input device, and a control system. The control system comprises one or more processors and a memory. The memory comprising programmed instructions adapted to cause the one or more processors to perform operations. The operations comprise determining an orientation of an end-effector reference frame relative to a field-of-view reference frame, determining an orientation of an input-device reference frame relative to a display reference frame, establishing an alignment relationship, and commanding (based on the alignment relationship) a change in a pose of the end effector in response to a change in a pose of the master input device. The end effector reference frame is defined for an end effector of a tool, and the field of view reference frame is moveable relative to the field-of-view reference frame and defined for a field of view of an imaging device. The input-device reference frame is defined for the master input device, and the display reference frame is defined for the image. The alignment relationship comprises an end-effector-to-field-of-view alignment relationship or an input-device-to-display alignment relationship, where the end-effector-to-field-of-view alignment relationship is between the end-effector reference frame and the field-of-view reference frame and is independent of a position relationship between the end-effector reference frame and the field-of-view reference frame, and where the input-device-to-display alignment relationship is between the input-device reference frame and the display reference frame and is independent of a position relationship between the input-device reference frame and the display reference frame.

In an aspect, a method for operating a medical system comprises determining an orientation of an end-effector reference frame relative to a field-of-view reference frame, determining an orientation of an input-device reference frame relative to a display reference frame, establishing an alignment relationship, and commanding (based on the alignment relationship) a change in a pose of the end effector in response to a change in a pose of the master input device. The end effector reference frame is moveable relative to the field-of-view reference frame and is defined for an end effector of a tool, and the field of view reference frame is defined for a field of view of an imaging device. The input-device reference frame is defined for a master input device of the medical system, and the display reference frame is defined for a display of the medical system. The alignment relationship comprises an end-effector-to-field-of-view alignment relationship or an input-device-to-display alignment relationship, where the end-effector-to-field-of-view alignment relationship is between the end-effector reference frame and the field-of-view reference frame and independent of a position relationship between the end-effector reference frame and the field-of-view reference frame, and where the input-device-to-display alignment relationship is independent of a position relationship between the master input device reference frame and the display reference frame.

In an aspect, a teleoperated system comprises a display, a master device, and a control system. A display reference frame is defined for the display, a and a master-device reference frame is defined for the master device. The control system comprises a memory storing instructions that, when executed by the control system, cause the control system to perform operations. The operations comprise: determining a complete orientation of a field-of-view reference frame, determining a complete orientation of an end effector reference frame, determining a complete orientation of the display reference frame, determining a complete orientation of the master-device reference frame, establishing a teleoperated master/slave control relationship between the master device and the end effector, and executing the master/slave control relationship between the master device and the end effector. The field-of-view reference frame is defined for a field of view of an imaging device, and the end-effector reference frame is defined for an end effector of a tool. Establishing the teleoperated master/slave control relationship comprises establishing an alignment relationship. The alignment relationship comprises an end-effector-to-field-of-view alignment relationship or a master-device-to-display alignment relationship, where the end-effector-to-field-of-view alignment relationship is between the end-effector reference frame and the field-of-view reference frame and is based on less than complete position information relating the end-effector reference frame and the field-of-view reference frame, and where the master-device-to-display alignment relationship is between the master device reference frame and the display reference frame and is based on less than complete position information relating the master-device reference frame and the display reference frame. Executing the master/control relationships comprises changing a pose of the end effector corresponding to a change in a pose of the master device.

In an aspect, the alignment relationship is between the master-device reference frame and the display reference frame and is based on: the complete orientation of the master device reference frame, the complete orientation of the display reference frame, and less than complete position information relating the master device reference frame and the display reference frame.

In an aspect, a telesurgical system comprises means to determine a complete orientation of a field of view reference frame, means to determine a complete orientation of an end effector reference frame, means to determine a complete orientation of a display reference frame of a display on which an image of the end effector is displayed when the surgical end effector is within the field of view of the endoscopic camera, means to determine a complete orientation of a master device reference frame of a master device, means to establish a teleoperated master/slave control relationship between the master device and the surgical end effector, and means to execute the master/slave control relationship between the master device and the end effector. The field of view reference frame is defined for a field of view of a imaging device, and the end effector reference frame is defined for a surgical end effector. The means to establish the teleoperated master/slave control relationship establishes such relationship by establishing an alignment relationship between the master device reference frame and the display reference frame. The alignment relationship between the master device reference frame and the display reference frame is based on the complete orientation of the master device reference frame and the complete orientation of the display reference frame, and is independent of a position relationship between the master device reference frame and the display reference frame. The means to executing the master/control relationship executes such relationship by changing a pose of the end effector corresponding to a change in a pose of the master device.

In an aspect, a non-transitory machine-readable medium comprises a plurality of machine-readable instructions which when executed by one or more processors associated with a medical device are adapted to cause the one or more processors to perform any of the operations or methods described herein.

The aspects described herein may further comprise none, any one, or any combination of the following.

In some aspects, the alignment relationship comprises the end-effector-to-field-of-view alignment relationship. In some aspects, the alignment relationship comprises the master-device-to-display alignment relationship.

In some aspects, the alignment relationship is a first alignment relationship, and the operations further comprise establishing a second alignment relationship, where the second alignment relationship comprises the input-device-to-display alignment relationship where the first alignment relationship comprises the end-effector-to-field-of-view alignment relationship, and where the second alignment relationship comprises the end-effector-to-field-of-view alignment relationship where the first alignment relationship comprises the input-device-to-display alignment relationship where the alignment relationship.

In some aspects, the operations (or method) further comprise establishing a teleoperated master-slave control relationship based on the alignment relationship.

In some aspects, determining an orientation of an end effector reference frame relative to a field of view reference frame comprises: determining a complete orientation of the field of view reference frame, and determining a complete orientation of the end effector reference frame. In some aspects, determining an orientation of a master input device reference frame relative to a display reference frame comprises: determining a complete orientation of the display reference frame, and determining a complete orientation of the master input device reference frame.

In some aspects, the operations (or method) do not comprise determining the complete position of at least one reference frame selected from the group consisting of: the field of view reference frame, the end effector reference frame, the display reference frame, and the master input device reference frame. In some aspects, the operations (or method) do not comprise determining a complete position of the end effector reference frame relative to the field of view reference frame. In some aspects, the operations (or method) do not comprise determining a complete position of the master input device reference frame relative to the display reference frame. In some aspects, the operations (or method) further comprise determining less than a complete position of the end effector reference frame relative to the field of view reference frame. In some aspects, the operations (or method) further comprise determining less than a complete position of the master input device reference frame relative to the display reference frame.

In some aspects, the system is a teleoperated medical system, and the tool is a medical tool. In various aspects, the medical tool is a diagnostic tool or a treatment tool. In some aspects, the system is a telesurgical system, and the tool is a surgical tool.

In some aspects, the system further comprises a manipulator arm configured to removably support the tool, the manipulator arm comprising a plurality of joints and a plurality of links. In some aspects, commanding the change in the pose of the end effector comprises using or commanding the manipulator arm to change the pose of the end effector.

In some aspects, establishing the alignment relationship comprises: establishing the alignment relationship in response to an indication to begin teleoperation. In some aspects, the indication to begin teleoperation comprises receiving a user command to begin teleoperation. In some aspects, the indication to begin teleoperation comprises an exit from a clutch mode. In some aspects, in the clutch mode the master-slave control relationship is temporarily suspended. In some aspects, in the clutch mode the control system does not command the change in a pose of the end effector in response to the change in the pose of the master input device.

In some aspects, the operations (or method) further comprise: updating the alignment relationship. In some aspects, updating the alignment relationship comprises: updating the alignment relationship while executing the master/slave control relationship. In some aspects, updating the alignment relationship comprises: updating the alignment relationship at a predetermined time interval.

In some aspects, the system is a telesurgical system comprising the imaging device and the tool having the end effector. The imaging device comprises an endoscopic camera, and the tool comprises a surgical tool.

In some aspects, less than complete position information is no position information relating the master device reference frame and the display reference frame. In an aspect, less than complete position information is partial position information relating the master device reference frame and the display reference frame.

In some aspects, the operations (or method) further comprise determining partial position information of at least one reference frame. The reference frame is selected from the group consisting of: the field of view reference frame, the end effector reference frame, the display reference frame, and the master device reference frame.

In some aspects, changing a pose of the end effector corresponding to a change in a pose of the master device comprises: changing a direction of movement of the end effector corresponding to a change in direction of movement of the master device.

In some aspects, the system further comprises means to determine spatial position between two or more units of the system, or further comprise a spatial determining system, incorporating one or more of: a temporary localized mechanical relationship between a pair of teleoperated system units, a fixed-sensor locator system, a fixed-feature locator system, a simultaneous localization and mapping system, a machine vision system that uses images from the imaging device, an optical fiber shape sensor, an accelerometer, a magnetometer, a gyroscope, a vibration detector, and a vibration injector.

Implementations and aspects are often described in terms of a telesurgical system, but they are not limited to telesurgical systems. Implementations in various other teleoperated systems are contemplated, including without limitation teleoperated systems with military, research, material handling applications, safety, emergency, and manufacturing applications. Thus, the techniques disclosed apply to medical and non-medical procedures, and to medical and non-medical tools (e.g., manipulation tools or cameras). For example, the cameras or other tools, systems, and methods of any of the embodiments described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques can also be used for medical treatment or diagnosis procedures that do, or do not, include surgical aspects.

BRIEF DESCRIPTION OF THE DRAWINGS

FIGS. 5A-5J are schematic views of various teleoperated system architectures, spatial alignments, and associated control aspects.

DETAILED DESCRIPTION

Figure 1:
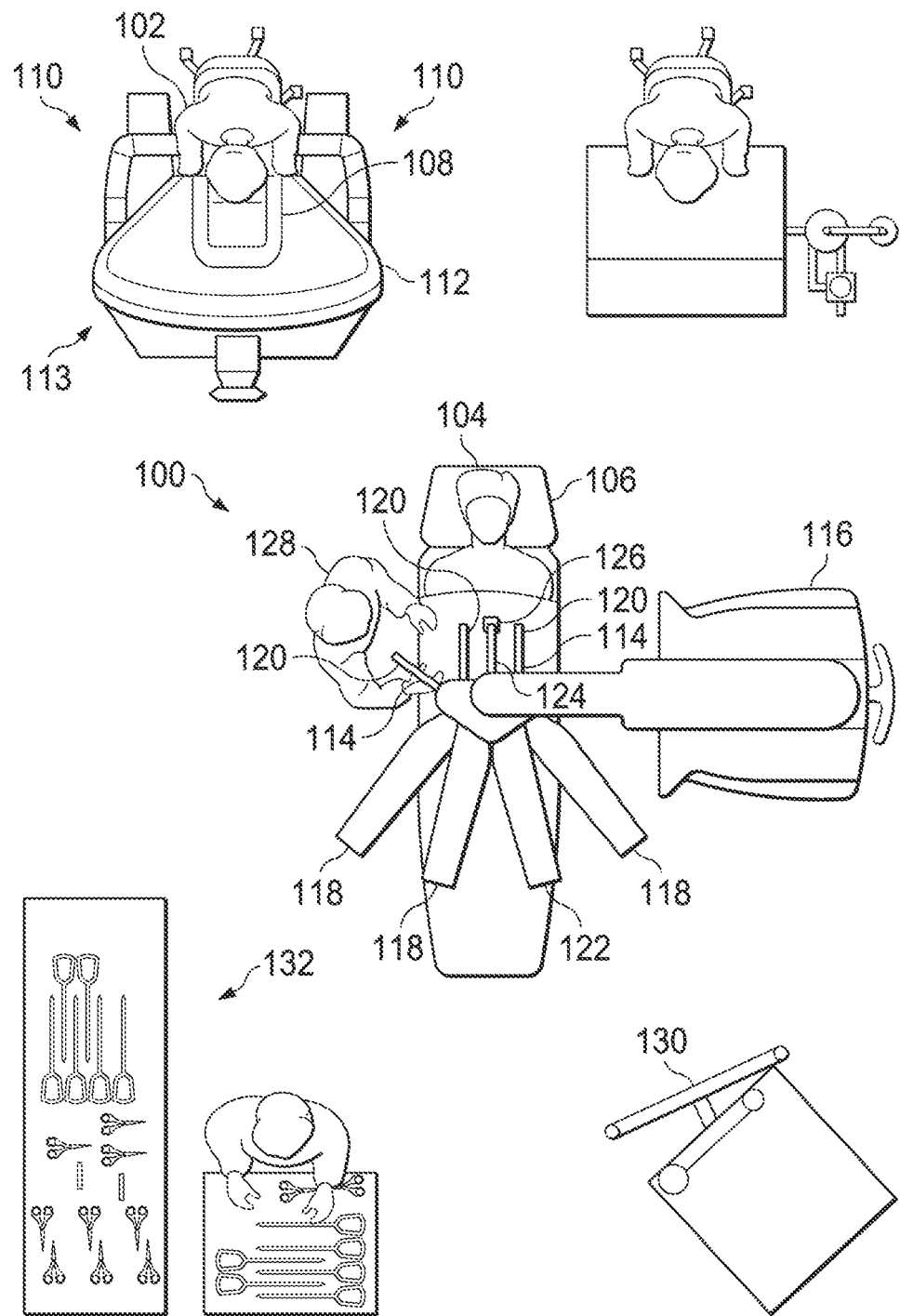
FIG. 1 is a diagrammatic plan view of a telesurgical system.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various special device positions and orientations. The combination of a body's position and orientation define the body's "pose."

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. The words "including" or "having" mean including but not limited to.

It should be understood that although this description is made to be sufficiently clear, concise, and exact, scrupulous and exhaustive linguistic precision is not always possible or desirable. For example, considering a video signal, a skilled reader will understand that an oscilloscope described as displaying the signal does not display the signal itself but a representation of the signal, and that a video monitor described as displaying a signal does not display the signal itself but the video information the signal carries.

In addition, the singular forms "a", "an", and "the" are intended to include the plural forms as well, unless the context indicates otherwise. And, the terms "comprises", "includes", "has", and the like specify the presence of stated features, steps, operations, elements, and/or components but do not preclude the presence or addition of one or more other features, steps, operations, elements, components, and/or groups. And, the or each of the one or more individual listed items should be considered optional unless otherwise stated, so that various combinations of items are described without an exhaustive list of each possible combination. The auxiliary verb may likewise imply that a feature, step, operation, element, or component is optional.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Elements described as coupled (e.g., mechanically, electrically, in communication, and the like) may be directly coupled, or they may be indirectly coupled via one or more intermediate components unless otherwise specified.

Inventive aspects are described in part in terms of an implementation using a da Vinci® Surgical System, commercialized by Intuitive Surgical, Inc. of Sunnyvale, California. Examples of such surgical systems are the da Vinci X® Surgical System (Model IS4200), the da Vinci Xi® Surgical System (Model IS4000), and the da Vinci Si® Surgical System (Model IS3000). Knowledgeable persons will understand, however, that inventive aspects disclosed herein may be embodied and implemented in various ways, including computer-assisted and hybrid combinations of manual and computer-assisted embodiments and implementations. Implementations on da Vinci® Surgical Systems are merely exemplary and are not to be considered as limiting the scope of the inventive aspects. For example, the techniques disclosed apply to medical and non-medical procedures, and to medical and non-medical tools (e.g., manipulation tools or cameras). For example, the tools (e.g., manipulation tools or cameras), systems, and methods of any of the embodiments described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques can also be used for medical treatment or diagnosis procedures that do, or do not, include surgical aspects.

Persons of skill in the art will understand that a computer is a machine that follows programmed instructions to perform mathematical or logical functions on input information to produce processed output information. A computer includes a logical calculation unit that performs the mathematical or logical functions, and a memory system that stores the programmed instructions, the input information, and the output information. The term "computer" and similar terms, such as "processor" or "controller" or "control system", should be considered synonymous. Persons of skill in the art will understand that a computer's function may be centralized or distributed among two or more locations, and it may be implemented in various combinations of hardware, firmware, and software.

Teleoperated medical systems have been developed that increase an operator's dexterity or ability, to improve ergonomics, etc. For example, minimally invasive teleoperated surgical systems that operate at least in part with computer assistance ("telesurgical systems") have been developed and operate using a master/slave model in which a user-operated master input device controls a motor-driven slave surgical tool. The user grasps and moves the master input device to operate a slave surgical tool by remote control, rather than directly holding and moving the tool by hand. The slave surgical tool follows the motion of the master input device.

During minimally invasive telesurgery, an imaging device such as an endoscopic camera at the surgical site captures a moving image of tissue and a slave surgical tool's working end. For convenience, "camera" is used herein to refer generally to imaging devices used to capture one or more images. Examples of image devices include those based on optical, ultrasound technology, magnetic resonance imaging (MRI), CT (computed tomography), X-ray, etc. Examples of endoscopic cameras include monoscopic, stereoscopic, and 3D cameras, as well as cameras that image inside the visible spectrum, in the infrared, in the ultraviolet, some other part of the spectrum, or a combination of the foregoing. "Tool" is used herein to include imaging and non-imaging instruments. The term "end effector" as used herein refers to any distal end component or portion of a tool, such as a tip of a manipulation, suction, irrigation, or cautery tool or a tip of an imaging device such as an endoscopic camera (e.g., examples of end effectors include a grasper, scissors, a cautery hook, a suction/irrigation nozzle, a blunt tip, a distal tip of a catheter or other flexible device, lenses for an optical imaging device, a probe tip for an ultrasonic imaging device, etc.). The user views the image while operating the master device and sees the slave end effector movement that corresponds to the master device movement. A computer control system provides the control interface between the master device and the slave surgical tool.

The user typically operates the master device from a position that is remote from the patient (e.g., across the operating room, in a different room, or in a completely different building from the patient). In many telesurgical situations, the user is outside the sterile field and so does not directly interact with the patient. In some telesurgical situations, however, the user operating a master device is close enough to the patient to directly interact with the patient, optionally within the sterile field. The master device is typically free to move in all six Cartesian degrees of freedom (DOFs), so that changes in master device position (translations along the Cartesian axes) and changes in master device orientation (rotations around the Cartesian axes) result in corresponding slave tool translations and rotations. This description is in the context of Cartesian reference frames, and persons of skill in the art will understand that other suitable three-dimensional reference systems (e.g., cylindrical, spherical) may be used.

The master device may be in various forms. For example, the master device may be the distal-most link in a kinematic chain with redundant mechanical DOFs, a joy-stick, an exoskeletal glove, or the like. In some instances the master device tracks hand gestures, so that the user's hand alone, or part of the user's hand, functions as a virtual master device if the hand's translations and rotations are tracked with sufficient accuracy for surgery. Master devices may optionally have one or more mechanical DOFs to control corresponding end effector mechanical DOFs, such as a pincer mechanism for end effector jaw grip, or a switch (e.g., push button or slider) for end effector knife movement between jaws. And, master devices may optionally have one or more inputs such as switches to control additional end effector or surgical system features, such as electrosurgical energy application, stapler control, engaging and disengaging the master/slave control relationship between the master device and the slave tool ("clutching"), changing system operating modes, changing master device control from one slave surgical tool to a second slave surgical tool, display menu selection, and the like.

Surgical tools are in various forms, and they include tools for both therapeutic and diagnostic functions. Example surgical tools include tissue graspers, needle drivers, scissors, retractors, electrosurgical cautery tools, staplers, surgical clip appliers, ultrasonic cutters, suction/irrigation tools, catheters, ultrasound probes, etc. In some situations a camera, such as an endoscopic camera or other image capture technology, may be considered a surgical tool. Cameras and associated image processing technology may be used for specialized functions, such as near infra-red image capture, fluorescent energy capture, hyperspectral imaging, and the like. These special imaging functions increase the effectiveness of an intervention.

Many telesurgical systems incorporate robotic technology (they are often referred to as "surgical robots" even though they may undertake no autonomous action). Example telesurgical systems are illustrated in U.S. Pat. No. 6,331,181 B1 (filed Oct. 15, 1999)(describing a multi-port system in which a camera and other surgical tools enter the body via separate ports), U.S. Pat. No. 8,784,435 B2 (filed Aug. 12, 2010)(describing a single-port system in which a camera and other surgical tools enter the body via a single common port), and U.S. Pat. No. 8,801,661 B2 (filed Nov. 7, 2013) (describing a system that uses a flexible surgical tool). The full disclosures of U.S. Pat. Nos. 6,331,181, 8,784,435, and 8,801,661 are incorporated herein by reference in their entireties.

Telesurgical systems typically include one or more motor-driven teleoperated manipulators. A surgical tool is removably mounted on a manipulator, and the manipulator typically moves both the tool as a whole and component parts of the tool, including the tool's end effector. The manipulator's movements correspond to the user's master device movements so that the end effector movements precisely follow the master device movements. Various telesurgical manipulator architectures are known, such as serial kinematic chains, spherical linkages, orthogonal prismatic joints (both linear and circular curvilinear), and the like. The surgical tool itself may be a single rigid body or a kinematic chain, and so the tool's kinematic pose determines its end effector's pose in space. Likewise, the manipulator's kinematic pose determines the surgical tool's pose in space.

The manipulator is typically held in a fixed position and orientation by a non-teleoperated setup structure, such as a kinematic arm. The setup structure typically includes at least one kinematic pair of links coupled by a movable and lockable joint, so that the manipulator may be repositioned in space and then held in the new pose. The lockable joint(s)

may be powered (motorized) or unpowered. And the lockable joint(s) may be locked in various ways, such as by using manually or electrically controlled brakes, or by controlling a powered joint to maintain a fixed relationship between links in a kinematic pair. The setup structure's kinematic pose determines the manipulator's pose in space by holding the manipulator's proximal-most ("base") link stationary.

In turn, the setup structure may have a proximal-most link ("base") optionally fixed to a mechanical ground (e.g., floor, wall, ceiling, or structure fixed to floor, wall, or ceiling) or optionally movable with reference to a mechanical ground (e.g., a cart that rolls on the floor, moves along one or more rails on a wall, ceiling, or operating table, etc.). A movable setup structure base also functions to pose the manipulator in space. The manipulator, the optional setup structure (fixed or movable), and the optional base (fixed or movable) function together as a support structure for the surgical tool mounted on the manipulator with reference to the mechanical ground. Any structure that holds a manipulator, an imaging device such as a camera, or another tool fixed in space with reference to a mechanical ground may function as a support structure. For example, a motorized or no-motorized fixture holding an endoscopic camera steady in space may function as camera support structure as the camera captures images of the surgical site. As another example, an endoscopic camera may be held in place by support structure comprising a kinematic chain; the kinematic chain may be a passive kinematic chain, or include one or more driven joints. Additional examples of mechanical support structures are described below.

FIG. 1 is a diagrammatic plan view that shows components of an exemplary teleoperated system, specifically a multi-port telesurgical system 100 for performing minimally invasive surgery. System 100 is similar to that described in more detail in U.S. Pat. No. 6,246,200 B1 (filed Aug. 3, 1999)(disclosing "Manipulator Positioning Linkage for Robotic Surgery), the full disclosure of which is incorporated herein by reference. Further related details are described in U.S. Pat. No. 8,529,582 B2 (filed May 20, 2011)(disclosing "Instrument Interface of a Robotic Surgical System") and U.S. Pat. No. 8,823,308 B2 (filed Jul. 1, 2011)(disclosing "Software Center and Highly Configurable Robotic Systems for Surgery and Other Uses"), the full disclosures of which are likewise incorporated herein by reference. A system user 102 (typically a surgeon or other skilled clinician when system 100 is used for surgery) performs a minimally invasive surgical procedure on a patient 104 lying on an operating table 106. The system user 102 sees moving images (monoscopic (2D) or stereoscopic (3D)) presented by display 108 and manipulates one or more master devices 110 at a user's control unit 112. In response to the user's master device movements, a computer 113 acts as a specialized control system and directs movement of slave teleoperated tools 114 (the tool 114 being a surgical tool in this surgical example). As described in more detail below, master devices 110 are computationally aligned with tools 114. Based on this alignment, computer 113 generates commands that correlate the movement of the master devices and the end effectors of tools 114 so that the motions of the end effectors follow the movements of the master devices in the hands of the system user 102 in a way that is intuitive to the user.

As described above, computer 113 typically includes data processing hardware and machine-readable code that embodies software programming instructions to implement methods described herein (e.g., including related control systems). And although computer 113 is shown as a single block in the simplified diagram of FIG. 1, the computer may comprise two or more centralized or distributed data processing units, with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or it may be integrated into various other telesurgical system components.

As shown in FIG. 1, system 100 further includes a manipulator assembly 116, which includes two teleoperated manipulators 120 for tools 114 and teleoperated manipulator 124 for a tool that comprises an imaging device. For convenience of explanation, the imaging device is shown and described below as a camera 126, and camera 126 may be any appropriate imaging device. For example, camera 126 may be configured to image optically, ultrasonically, or using any other appropriate technology. In this surgical example, camera 126 is an endoscopic camera configured to image in the visible spectrum. Other numbers and combinations of manipulators are optional (e.g., one, three, or more manipulators for tools, two or more manipulators for cameras). Manipulator assembly 116 also includes manipulator setup structures 118 that support manipulators 120 during the procedure. And, manipulator assembly 116 includes an imaging device setup structure shown as a camera setup structure 122; camera setup structure supports manipulator 124. The tool setup structures and the camera setup structure each have a base link, and these base links are coupled to a single movable cart. For each tool 114 and for camera 126, the associated manipulator, setup structure, and cart illustrate a support structure for the tool or camera.

As shown, the image of the internal surgical site is displayed to user 102 by a display 108 in user's control unit 112. The internal surgical site is optionally simultaneously shown to assistant 128 by an auxiliary display 130 (2D or 3D). As mentioned above and described in more detail below, however, in some teleoperated systems user 102 may be close to patient 104 during surgery (e.g., in a position similar to assistant 128's position as shown). In these telesurgical system architectures the user may view the image of the surgical site on a 2D or 3D display mounted on the floor, wall, ceiling, or other equipment, as illustrated by display 130's position.

Sterile assistant 128 (e.g., a nurse, an assisting surgeon, or another skilled clinician) performs various optional tasks before, during, and after surgery. For example, assistant 128 may adjust the poses of manipulators 120,124, adjust setup structures 118,122, swap tools 114 with other tools 132 on a manipulator, operate non-teleoperated medical tools and equipment within the patient, hold an endoscopic camera, and perform other tasks related to teleoperated surgery and surgery in general.

Figure 2:
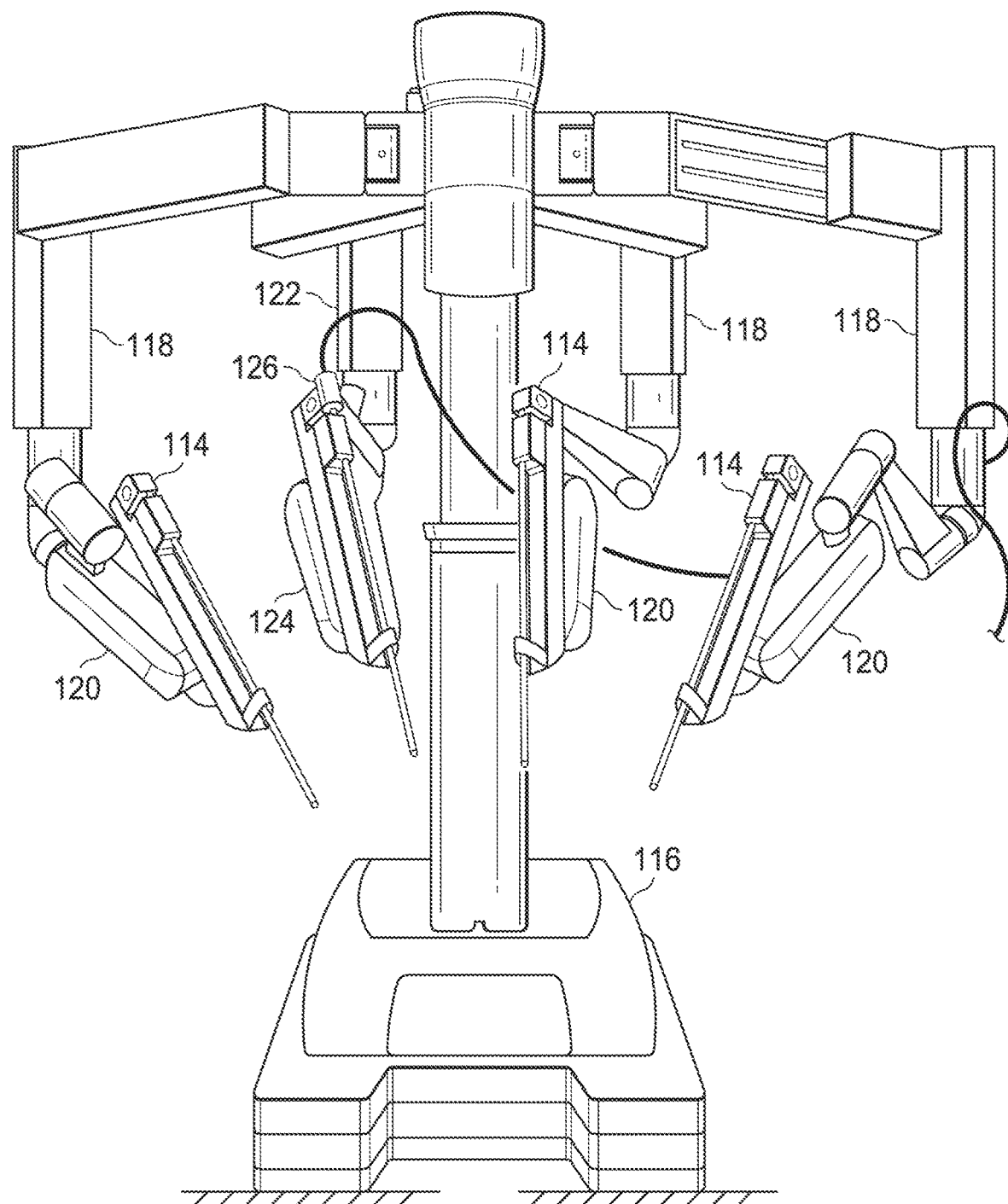
FIG. 2 is a front view of a telesurgical system patient-side unit.

FIG. 2 is a front view that illustrates a manipulator assembly 116. Specifically, FIG. 2 shows a telesurgical system patient-side unit that illustrates an embodiment of a multi-port telesurgical manipulator assembly, which is commercialized as a da Vinci® Surgical System by Intuitive Surgical, Inc. of Sunnyvale, California, U.S.A. In a multi-port telesurgical system, tools enter the body through two or more separate incisions or natural orifices. In this example, manipulator assembly 116 includes four teleoperated surgical tool and camera manipulators supported by a movable patient-side unit.

In other embodiments of a multi-port telesurgical system, one or more of the manipulators 120,124 and associated setup structures 118,122 are individually or in combination mounted on one or more separate movable units or are fixed to a mechanical ground as described herein. It can be seen that various combinations of manipulators and their associated support structures may be used.

In a single-port telesurgical system, all tools enter the body through a single incision or natural orifice. Examples of manipulator assemblies for single port telesurgical systems are shown and described in U.S. Pat. No. 8,784,435 B2 (filed Aug. 12, 2010) (disclosing "Surgical System Entry Guide"), and examples of telesurgical systems and flexible surgical tools are shown and described in U.S. Pat. No. 8,801,661 B2 (filed Nov. 7, 2013) (disclosing "Robotic Catheter System and Methods").

In accordance with an aspect of the invention, one or more master devices as described herein may be used to control two or more different telesurgical system configurations, be they two or more different multi-port systems, two or more multi-port, single-port systems, two or more flexible tool systems, or any combination of such multi-port, single-port, and flexible tool systems.

Figure 3:
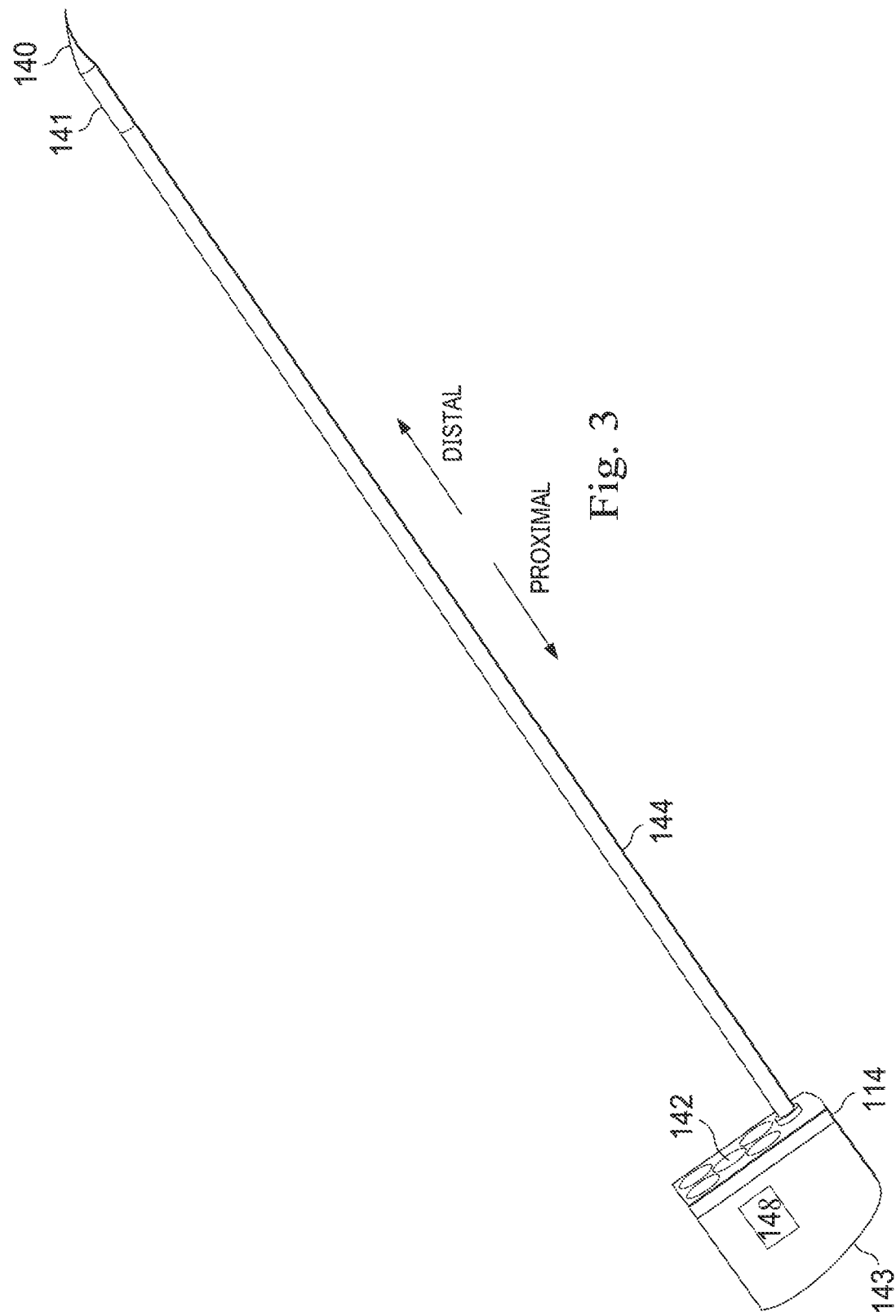
FIG. 3 is a perspective view of a teleoperated surgical tool.

FIG. 3 is a perspective view of a teleoperated tool 114 that may be used with a teleoperated system. Specifically, a teleoperated surgical tool is shown; this surgical tool that includes a distal end effector 140, an optional wrist 141, a proximal end chassis 142, a housing 143 over chassis 142 (chassis 142 and housing 143 may optionally be combined), and an elongate shaft 144 coupled between end effector 140 and chassis 142. End effector 140 is coupled to shaft 144 either directly or via optional wrist 141. Various wrist 141 architectures allow end effector 140's orientation to change with reference to shaft 144 in various combinations of pitch, yaw, and roll. Optionally, the end effector roll function is carried out by rolling shaft 144. Various mechanisms (combinations of pulleys, cables, levers, gears, gimbals, motors, etc.) are mounted on chassis 142 and function to receive either mechanical or electrical inputs from tool 114's associated manipulator. These inputs are used to orient and operate end effector 140. Chassis 142 will typically include a mechanical or electrical interface 146 adapted for coupling to a manipulator 120,124. As described in more detail in U.S. Pat. No. 6,331,181 B1, tool 114 will often include a memory 148, with the memory typically being electrically coupled to a data interface (the data interface typically forming a portion of interface 146). This data interface allows data communication between memory 148 and computer 113 (see FIG. 1) when the tool is mounted on the manipulator.

End effector 140 is also illustrative of an endoscopic camera-type tool with an image capture component at an appropriate location (such as the camera-type tool's proximal end or distal end), and either with or without wrist 141. And so, tool 114 by its structure also illustrates camera 126 for kinematic purposes, and subsequent reference to kinematic properties of, and control aspects associated with, tool 114 and its analogs apply as well to camera 126 and its analogs.

A variety of alternative teleoperated surgical tools of different types and differing end effectors 140 may be used. The tools associated with at least some of the manipulators are configured to be removed from their associated manipulator and replaced with an alternate tool during a surgical procedure. Additional details are provided in U.S. Pat. No. 8,823,308 B2.

In some operational environments, tools 114 and end effectors 140 optionally can be combined into combinations with multiple capabilities. Additional details related to these combinations are provided in U.S. Pat. No. 7,725,214 B2 (filed Jun. 13, 2007) (disclosing "Minimally Invasive Surgical System"), the disclosure of which is incorporated herein by reference in its entirety. Details related to interfaces between the tools 114 and the manipulators 120 are provided in U.S. Pat. No. 7,955,322 B2 (filed Dec. 20, 2006) (disclosing "Wireless Communication in a Robotic Surgical System") and U.S. Pat. No. 8,666,544 B2 (filed Jul. 10, 2013)(disclosing "Cooperative Minimally Invasive Telesurgical System"), the disclosures of which are incorporated herein by reference in their entireties, and also in U.S. Pat. No. 8,529,582 B2.

Figure 4:
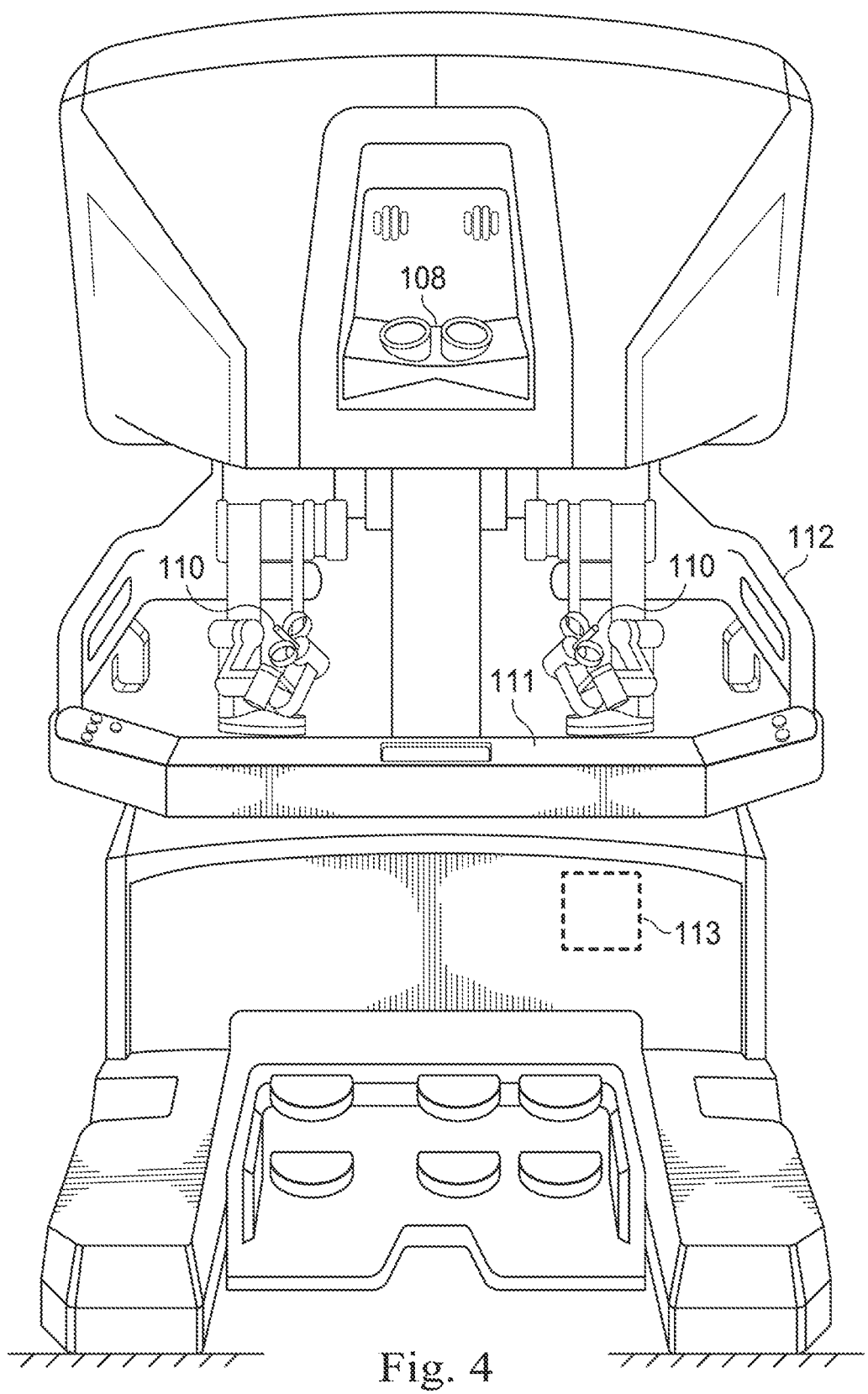
FIG. 4 is a front elevation view of a user control unit.

FIG. 4 is a front elevation view of a user control unit that shows an example of user control unit 112 of FIG. 1. The user control unit 112 includes a display 108 where an image of a work site (e.g. a surgical site in a surgical example) is displayed to a user 102 (e.g., a surgeon or other skilled clinician in the surgical example). A support 111 is provided on which the user 102 can rest the forearms while gripping two master devices 110, one in each hand. The master devices 110 are positioned in a space behind support 111 and generally below and behind display 108. When using control unit 112, the user 102 typically sits in front of control unit 112, positions the eyes in front of display 108, and grips the master devices 110, one in each hand, while resting the forearms on support 111. The master devices are positioned so that images of the associated end effectors are between the master devices and the eyes, so that motion of the master devices intuitively moves the masters as the user sees the end effectors in place of the hands. The user control unit 112 optionally may include the computer 113, or a portion of the computer 113, that functions to establish and maintain a teleoperated control relationship between the master devices 110 and the associated tools 114 and their end effectors 140.

An effective teleoperated control relationship between a master device and its slave tool (e.g. a slave surgical tool in the surgical example) and end effector requires a spatial alignment between the master device and the end effector. The alignment must provide a reasonably accurate relationship between the user's perceived motion of the master device (e.g., a proprioceptive sense) and the user's perceived resulting motion of the end effector (e.g., a visual sense). For example, if the user moves a hand grasping a master device to the left, the user expects to perceive the associated slave manipulator move to the left. If the perceived spatial motions match, then the user can easily control the slave's movement by moving the master device. But if the perceived spatial motions do not match (e.g., a master device movement to the left results in a slave movement up and to the right), then slave control is difficult. The required alignment is done using known kinematic relationships and reference frame transforms in the teleoperated system (e.g. a telesurgical system in the surgical example). These relationships are described below in Cartesian terms, although other 3-dimensional coordinate systems may be used for systems that function in 3-dimensional space.

1. Architectures and Reference Frames

Figure 5A:
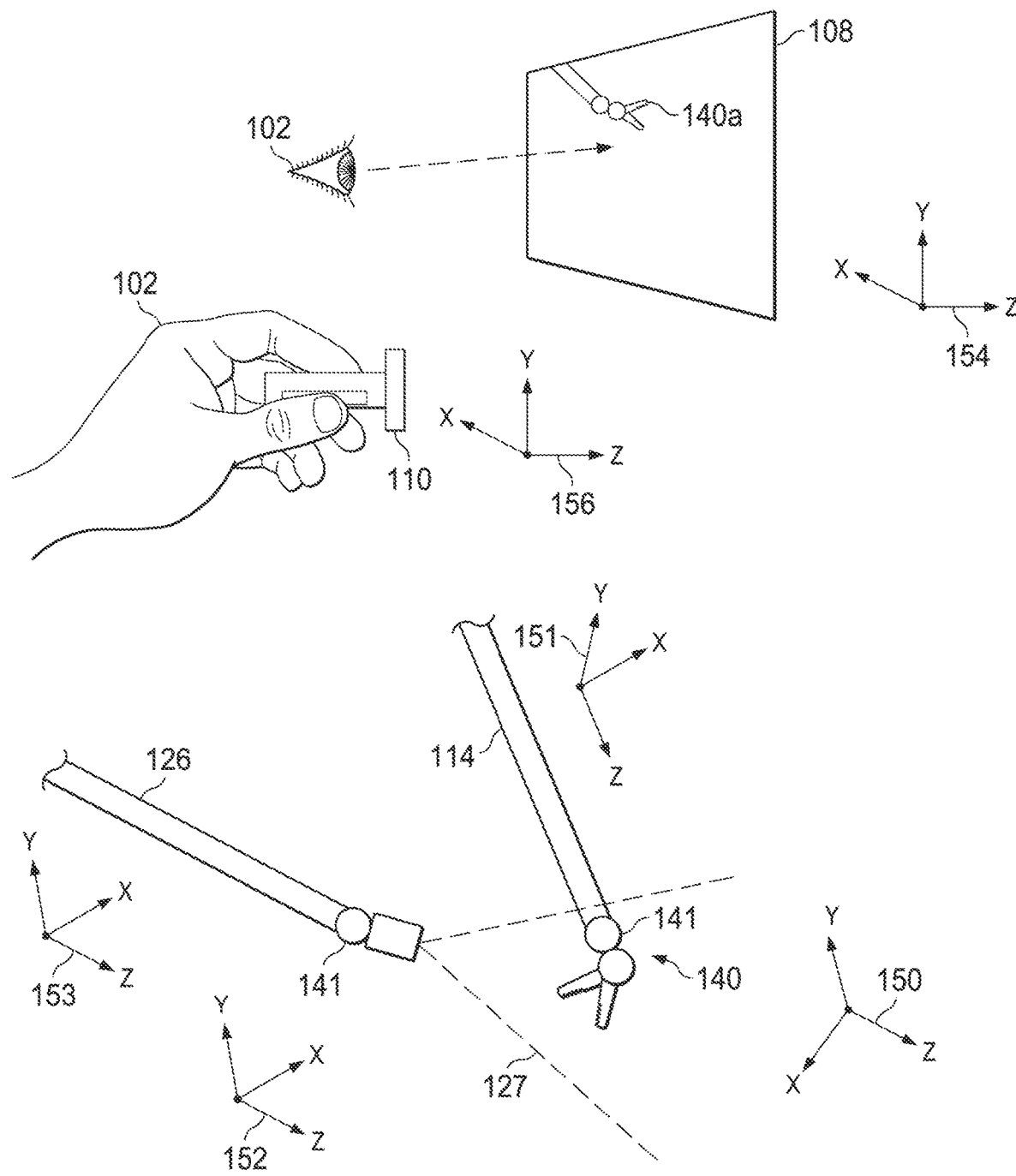

FIG. 5A is a schematic view of teleoperated system components (e.g. telesurgical system components in surgical examples) and associated Cartesian reference frames. As shown in FIG. 5A, camera 126 (e.g. an endoscopic camera in endoscopic surgery examples) has a field of view (FOV) 127. A distal portion of tool 114 (e.g. a surgical tool in surgical examples) with a wrist 141 and end effector 140, where its wrist 141 and its end effector 140 are within FOV 127. End effector reference frame 150 is associated with end effector 140, and tool reference frame 151 is associated with a proximal portion—the main body—of tool 114, such as the portion outside the patient (chassis, housing, proximal shaft, etc.). If the tool does not have a wrist 141, then reference frames 150 and 151 may be combined into a single reference frame sufficient to position and orient both the proximal portion and the end effector 140 of the tool 114, or the reference frames 150,151 may be kept separate, each having an origin at a different position. Similarly, field of view reference frame 152 is associated with FOV 127, and imaging device reference frame 153 is associated with a body portion of camera 126, such as the proximal portion outside the patient. If camera 126 does not have a wrist 141, then reference frames 152 and 153 may be combined into a single reference frame, or they may be kept separate, each having an origin at a different position.

For systems in which the physical dimensions of all tools 114 (e.g. surgical tools in surgical examples) including camera 126, and mechanical links are known, and in which all joint angles between these mechanical links can be determined (using direct rotation sensors, motor position sensors, optical fiber shape sensors, and the like), the kinematic relationship between reference frame 150 or 151 and a reference frame of any other link in tool 114 can be determined by using well-known kinematic calculations. Likewise, the kinematic relationship between reference frame 152 or 153 and any other link in camera 126 can be determined. And so, for such systems in which end effector 140 operates within FOV 127, an alignment between reference frames 150 and 152 will allow the user to easily control end effector 140 in FOV 127.

FIG. 5A further shows user 102 viewing display 108 and grasping master device 110. Display 108 displays the images within FOV 127. As shown, an image 140a of end effector 140 is displayed on display 108. A display reference frame 154 is associated with display 108, and a master device reference frame 156 is associated with master device 110. As master device 110 is translated and rotated in 3D space, its associated reference frame 156 translates and rotates correspondingly. These reference frame 156 translations and rotations (pose changes) can be sensed using known methods, and they are mathematically transformed to end effector 140's reference frame 150 to provide a control relationship between master device 110 and end effector 140 by using well-known kinematic calculations. As master device 110's frame 156 position and orientation is changed, end effector 140's reference frame 150 position and orientation is changed correspondingly, so that end effector 140's movement is slaved to master device 110's movement and follows master device 110's movement. User 102 views end effector 140's position and orientation changes on display 108. In order to establish the desired easy and intuitive control relationship between master device movement and end effector image movement, relationships are established between reference frames 150 and 152, and between reference frames 154 and 156. Once these reference frame relationships are established, movement of reference frame 150 with respect to reference frame 152 can be controlled to exactly or acceptably match movement of reference frame 156 with respect to reference frame 154.

Figure 5B:
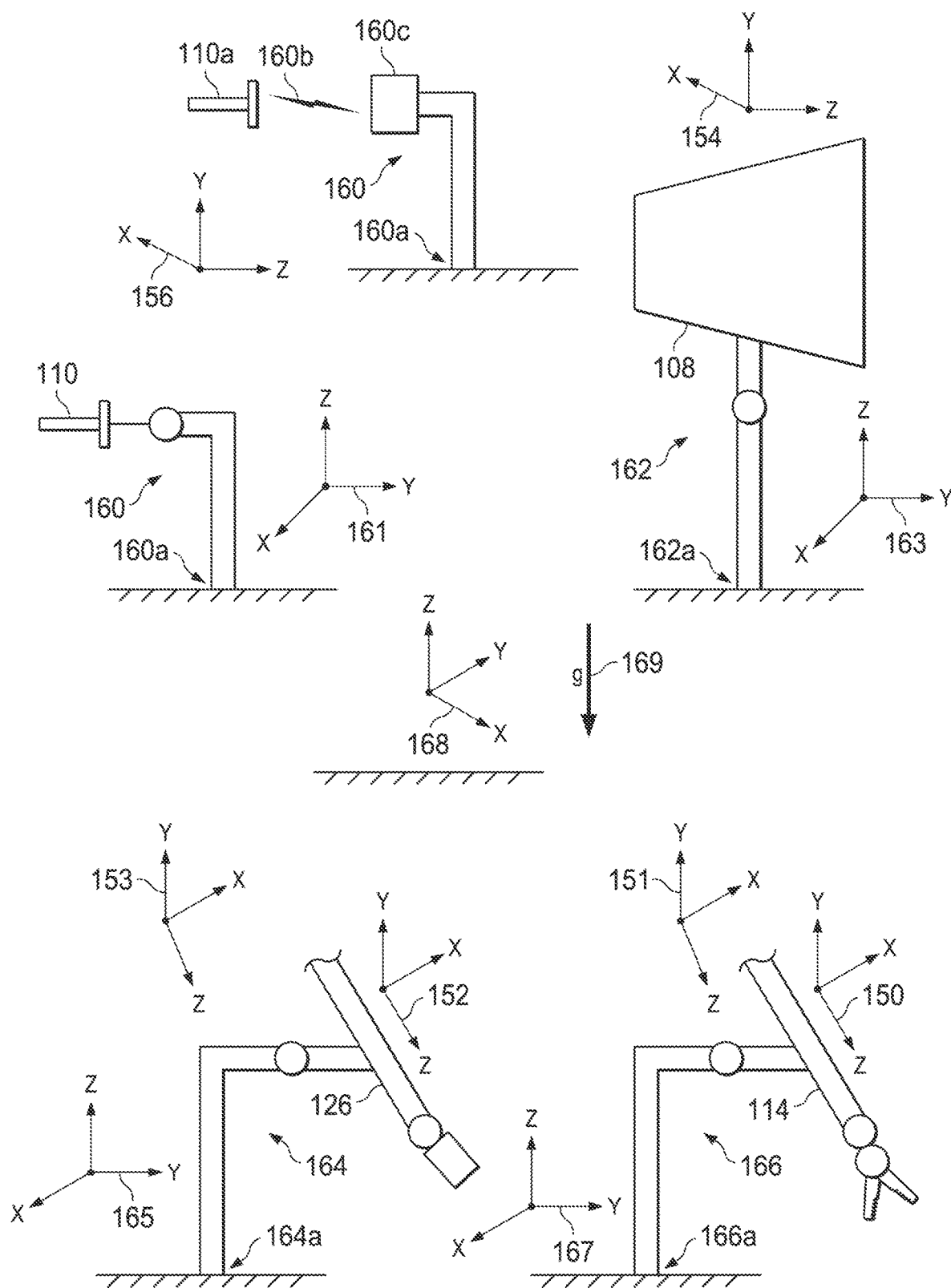

FIG. 5B is another schematic view of teleoperated system components and associated Cartesian reference frames. FIG. 5B illustrates the various components shown in FIG. 5A supported by mechanical support structures with reference to mechanical ground. FIG. 5B also illustrates reference frames associated with these support structures. For simplicity in this and the following figures, each support structure is depicted as a kinematic pair-two links coupled by a movable joint. It should be understood, however, that the support structures may be various optional configurations, such as a single link with zero DOF, a single kinematic pair with 1 or more DOFs, or combinations of kinematic pairs with 2 or more DOFs. And, support structures with 2 or more DOFs may optionally have joints that give the support structure redundant DOFs. Any of various kinematic joints (rotational as shown, prismatic, spherical, etc.) may be used.

As shown in FIG. 5B, master device 110 is supported by master device support structure 160 that begins at a mechanically grounded portion 160a (also called "base 160a") and extends distally until coupled with master device 110. Reference frame 161 is associated with one link of master device support structure 160. Similarly, display 108 is supported by display device support structure 162 that begins at a mechanically grounded base 162a and extends distally until coupled with display 108. Reference frame 163 is associated with one link of display device support structure 162. Similarly, camera 126 is supported by an imaging device support structure (shown as camera support structure 164) that begins at a mechanically grounded base 164a and extends distally until coupled with camera 126. Camera support structure reference frame 165 is associated with one link of camera support structure 164. And similarly, tool 114 is supported by tool support structure 166 that begins at a mechanically grounded base 166a and extends distally until coupled with tool 114. Reference frame 167 is associated with one link of tool support structure 166.

FIG. 5B also shows that master device support structure 160 may optionally be configured as a support structure when there is a break in the kinematic chain between master device 110a and the grounded portion 160a of the master device support structure. This configuration exists when master device 110 is not mechanically grounded (i.e., master device 110a is an "ungrounded" master device). For communication to or from master device 110a, tether that includes a communication line or a wireless connection may be used. It will be recalled that the master device may be the user 102's unaugmented hand or hands, and so spatial sensing of the hand pose is a wireless implementation of an ungrounded master. Control commands 160b from master device 110—position and orientation changes with reference to the master device reference frame 156 and any additional control inputs (buttons, levers, finger movements, hand poses, etc.) from the master device itself—are received via master device control input receiver 160c via the tether, via a wireless signal from the master device, or by free space pose sensing. The control commands are then routed to computer 113 for processing and corresponding slave control actions. Examples of ungrounded master devices are given in U.S. Pat. No. 8,521,331 B2 (filed Nov. 13, 2009) (disclosing "Patient-side Surgeon Interface for a Minimally Invasive, Teleoperated Surgical Instrument"), U.S. Pat. No. 8,935,003 B2 (filed Sep. 21, 2010)(disclosing "Method and System for Hand Presence Detection in a Minimally Invasive Surgical System"), and U.S. Pat. No. 8,996,173 B2 (filed Sep. 21, 2010)(disclosing "Method and Apparatus for Hand Gesture Control in a Minimally Invasive Surgical System"), which are incorporated herein by reference.

When joint positions are determined, well-known forward or inverse kinematic calculations are used to transform between master device reference frame 156 and master device support structure reference frame 161; between display reference frame 154 and display support structure reference frame 163; between the imaging device field-of-view reference frame (referred to as the camera FOV reference frame 152), the imaging device reference frame (camera reference frame 153), and the imaging device support structure reference frame (camera support structure reference frame 165); and between end effector reference frame 150, tool reference frame 151, and tool support structure reference frame 167. See e.g., U.S. Pat. No. 5,631,973 (filed May 5, 1994) (disclosing "Method for Telemanipulation with Telepresence"), U.S. Pat. No. 5,808,665 (filed Sep. 9, 1996)(disclosing "Endoscopic Surgical Instrument and Method for Use"), and U.S. Pat. No. 6,424,885 B1 (filed Aug. 13, 1999)(disclosing "Camera Referenced Control in a Minimally Invasive Surgical Apparatus"), the disclosures of which are incorporated herein by reference in their entireties.

FIG. 5B further shows a world reference frame 168 that is stationary with respect to the depicted mechanical grounds. Reference frame 168 may be directly associated with the mechanical grounds, or it may be associated with some other structure that remains stationary with respect to the mechanical grounds. And, gravity vector (g) 169 is illustrated with reference to world reference frame 168, arbitrarily aligned with frame 168's z-axis, although it should be understood that world reference frame may optionally be at any orientation in relation to the gravity vector. Magnetic north is another example of a reference axis that can be associated with a stationary world reference frame.

FIG. 5C is another schematic view of teleoperated system components and associated Cartesian reference frames. FIG. 5C illustrates that support structures for the system components may optionally be combined in various ways, and reference frames may be associated with the combined support structures. For example, the master device support structure 160 and the display device support structure 162 may be combined into a common control support structure 170 as shown. Control support structure 170 extends from a proximal base 170a at a mechanical ground and then branches distally to support display 108 and master device 110. An example of such a control support structure common to both a master device and a display is user control unit 112 shown in FIG. 4.

Control support structure 170 may also be configured to support ungrounded master device 110a configurations, as described above and as shown in FIG. 5C.

A control support structure reference frame 171 is associated with control support structure 170. Well-known forward or inverse kinematic calculations are used to transform between display reference frame 154, master device reference frame 156, and control support reference frame 171. And, control support reference frame 171 may be used in ungrounded master configurations as shown.

As another example that illustrates how support structures may optionally be combined, FIG. 5C shows camera support structure 164 and tool support structure 166 combined into a single device support structure 172 (e.g. a surgical device support structure in surgical examples). Device support structure 172 extends from a proximal base 172a at a mechanical ground and then branches distally to support tool 114 and camera 126. An example of such a device support structure is manipulator assembly 116 shown in FIG. 2.

A device support reference frame 173 is associated with device support structure 172. Well-known forward or inverse kinematic calculations are used to transform between end effector reference frame 150, tool reference frame 151, FOV reference frame 152, camera reference frame 153, and device support reference frame 173 as necessary. It will be recalled that in some cases a person may hold camera 126 and so act as a camera support structure.

FIG. 5C also shows world reference frame 168 and gravity vector (g) 169 in relation to control support structure 170 and device support structure 172, and also in relation to their associated reference frames. World reference frame 168 and gravity vector 169 are shown to illustrate they may be used as needed in relation to reference frames 171 or 173, as well as the various reference frames shown in FIG. 5B. Additional description is included below.

Persons of skill in the art will understand the various support structures may support a single object as shown, or optionally they may support two or more similar or dissimilar objects. For example, master device support structure 160 may support two master devices 110 (e.g., one master device 110 for each left and right hand to control corresponding individual tools 114, as illustrated by user control unit 112). Or, master device support structure 160 may support three or more master devices (e.g., two master devices 110 to control corresponding individual tools 114, and a third master device to control a third tool 114 or a camera 126). Combinations of one or more kinematically grounded master devices and one or more ungrounded master devices may be supported. And, if two or more master devices 110 are supported, display 108 may or may not be supported. Similarly, tool support structure 166 and device support structure 172 may support two or more tools 114, either with or without supporting camera 126 (e.g., the manipulator assembly 116).

In addition, teleoperated systems may optionally include combinations of two or more master device support structures 160, display device support structures 162, camera support structures 164, tool support structures 166, control support structures 170, and device support structures 172. For example, a da Vinci® Xi Surgical System has one control support structure 170 that supports a single display 108 and two master devices 110, and it has one device support structure that supports one endoscopic camera 126 and up to three tools 114. The da Vinci® Xi Surgical System optionally includes a second control support structure 170 that supports a second single display 108 and a second set of two master devices 110, and this second support structure may be used for example in training situations.

Persons of skill in the art will understand the various reference frames illustrated may optionally be combined in various ways to be a single reference frame when kinematically possible. For example, master device support reference frame 161 or control support reference frame 171 may be used as master device reference frame 156. Likewise, display reference frame 154 may be used as master device reference frame 156. Similarly, camera body reference frame 153 (the imaging device body reference frame) may be used as the FOV reference frame. To avoid needless description, all the various combinations are not listed, but all such combinations are within inventive aspects. In general, a reference frame associated with any link, including the distal-most link, in one kinematic chain may be used as a reference frame associated with any link, including the distal-most link, in a second kinematic chain. The kinematic relationship between the two reference frames is established as necessary in accordance with inventive aspects.

As described above, when display 108 and one or more master devices 110 are supported in a common control support structure 170, and when kinematic pose information about display and the master devices is determined, well-known kinematic calculations can be used to establish the required control alignment between reference frames associated with the display and one or more masters. This is because the position and orientation relationship between display 108, the one or more master devices 110, and the control support structure 170 is known. Similarly, when camera 126 and one or more tools 114 are supported in a common device support structure 172, well-known kinematic calculations can be used to establish the required control alignment between reference frames associated with the camera and its FOV, the one or more individual end effectors 140 corresponding to one or more individual tools 114, and the device control structure because the position and orientation relationship between these objects is known. To establish the control alignment required for teleoperation (e.g. for telesurgery in surgical examples), the control support reference frame 171 is transformed to the device support reference frame 173, and so the master/display and camera end effector/FOV reference frame alignment is established.

For example, new teleoperated system architectures may lack a single mechanical base common to the tools that can be used in determining the kinematic relationships among the tools. Similarly, new teleoperated system architectures may lack a mechanical base common to the master input devices that can be used to determine the kinematic relationships among the master input devices, or between the master input device(s) and other equipment such as a display. Thus, there is a need to for improved spatial registration and control in teleoperated systems.

For example, a teleoperated system may comprise two or more units that carry tools, where the units are moveable with reference to each other such that the kinematic relationship between units is not readily defined by being mounted to the same mechanical base. Further, a tool (such as a manipulation tool or a camera) may be supported by a passive support structure that is not instrumented with any sensors, or the tool may be held by a human, and so a computer control system is unable to determine the tool's kinematic information from the tool's support structure. Consequently, there is no single mechanical base common to these units that can be used to determine the kinematic relationships among the tools held by different units (e.g. among an endoscopic camera and one or more other medical tools, in a medical embodiment). In addition, one or more units may be added or removed as needed during a procedure (e.g. during a surgical procedure in surgical examples).

A similar situation may exist with master control devices used to control motion of the tools in these new systems. Master control devices may not share a common mechanical base, and the kinematic relationship between a display (e.g. one showing an image of a work site captured by an imaging device) and one or more master control devices (e.g. master input devices used to control the pose of one or more tools, such as one or more manipulation or imaging tools) may not be determinable from kinematic data alone. In addition, one or more master input devices may be added or removed as needed during a procedure.

Thus, in a situation in which one or more individual master device, display, imaging device, and tool support structures is used, however, the position and orientation relationship between the masters and the display, and between the imaging device and the other tools, is more difficult to establish. If position and orientation are to be used to establish the required control alignment, then both the position and the orientation of each separate support structure must be determined. And further, if the position or orientation of a separate support structure changes during use (e.g. for surgery in surgical examples), the new position and orientation of the changed support structure must be determined to again establish the required control alignment.

But, it is often difficult to determine the position and orientation of the separate support structures with sufficient accuracy.

Figure 5D:
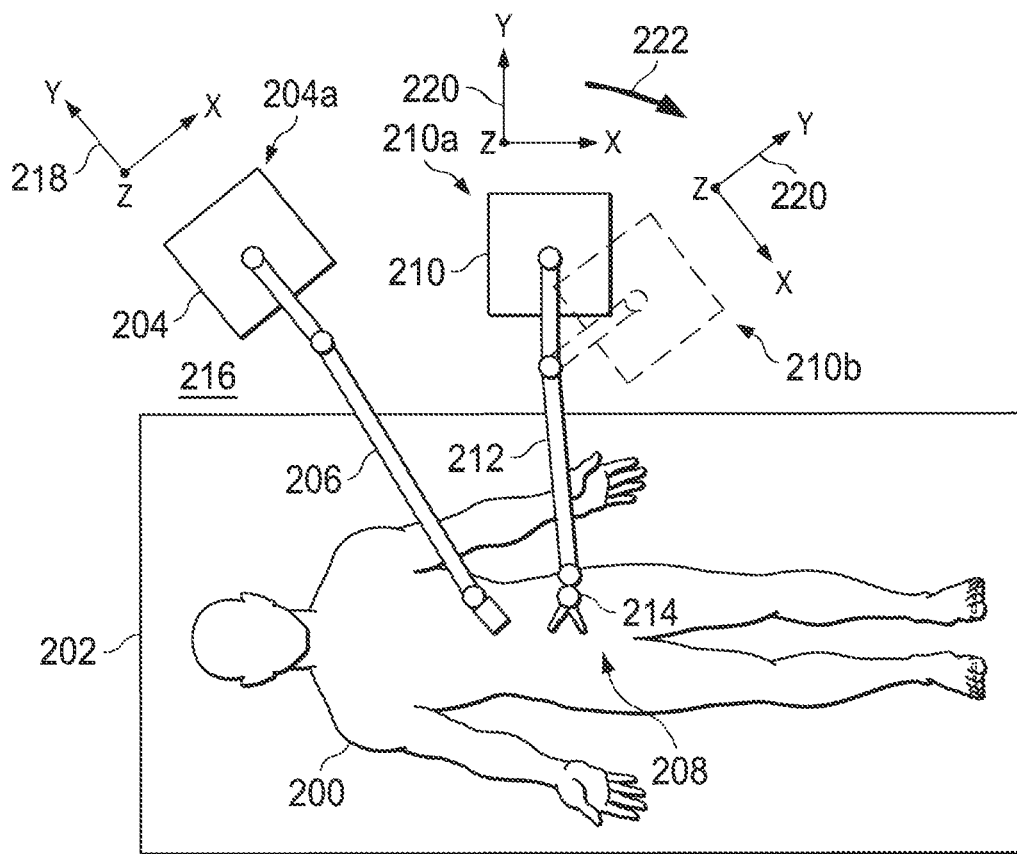

FIG. 5D is a schematic plan view of a medical example, showing a patient and two patient-side units that illustrates an example situation in which separate camera and tool support structures are used during a medical procedure. A patient 200 is shown on an operating table 202. An illustrative camera support structure 204 is shown as a mobile unit that can be moved across the operating room floor. As described above, camera support structure 204 supports endoscopic camera 206, which has an FOV posed toward work site 208 (a medical site such as a surgical site in this example) within the patient. An illustrative tool support structure 210 is included, also shown as a mobile unit that can be moved across the operating room floor. Tool support structure 210 supports tool 212, which is posed to locate its end effector 214 at the surgical site within the patient and the FOV. Camera support structure 204 represents a single camera support structure supporting a single camera, a single camera support structure supporting two or more cameras, and two or more individual camera support structures each supporting one or more cameras. Likewise, tool support structure 210 represents a single tool support structure supporting a single tool, a single tool support structure supporting two or more tools, and two or more individual tool support structures each supporting one or more tools. Further, camera support structure 204 and tool support structure 210 optionally represent combined device support structures as described above. Thus, to avoid a needlessly long description of all the possible variations, persons of skill in the art will understand the description that follows about camera support structure 204 and tool support structure 210 also applies to the various other support structures each may represent.

As shown, camera support structure 204 is at a certain pose 204a with reference to a mechanical ground (in this example, the floor 216). Camera support structure reference frame 218 is associated with an individual link of the camera support structure's kinematic chain (e.g., the base link at the mechanical ground, a link of a setup structure, a link of the manipulator, a link of the camera itself; the pose of the camera's distal-most link, which may be the camera body itself, is used also define the camera FOV's reference frame). The camera support structure reference frame 218 orientation changes as the associated individual link orientation changes, and kinematic calculation is then used to determine the orientation of any other link in the camera support structure.

This changing orientation aspect is further shown in FIG. 5D for tool support structure 210, which is shown at a first pose 210a with reference to the mechanical ground (floor 216). Tool support structure reference frame 220 is associated with an individual link of the tool support structure's kinematic chain (e.g., the base link at the mechanical ground, a link of a setup structure, a link of the manipulator, a link of the tool itself, including the end effector). FIG. 5D further shows tool support structure 210 at a second optional pose 210b with reference to the mechanical ground, which illustrates that the tool support structure may be placed at various positions and orientations for and during teleoperation (e.g. during telesurgery in surgical examples). Reference frame 220 changes as its associated link on the tool support structure changes, as shown by arrow 222. Persons of skill in the art will understand that the various poses of tool support structure 210 as shown also represent various poses of one or more additional individual or combined tool structures, as well as optional poses of camera support structure 204 and optionally one or more additional individual or combined camera support structures, as well as one or more camera and tool support structures combined into one or more separate individual device support structures. But, for all these optional combinations, the support structure that supports the camera is separate from the support structure that holds the tool that requires registration in the camera's FOV reference frame.

Figure 5E:
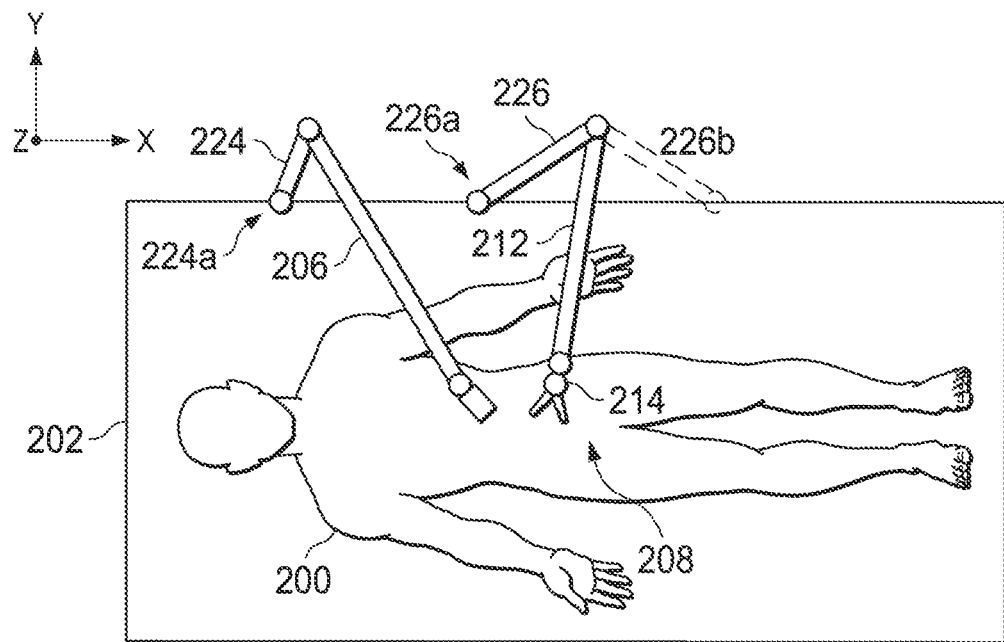

FIG. 5E is another schematic plan view of a patient and two patient-side units that shows a second example of changing orientation for separate camera and tool support structures. In FIG. 5E, the camera and tool support structures are mounted on the table 202 (e.g., medical table in medical examples, such as surgical tables in surgical examples). For example, the camera and tool support structures may be mounted at various positions along the table's side rail(s)), which serves as a mechanical ground. Camera support structure 224 for camera 206 is mounted to table 202 at base position 224a. Similarly, tool support structure 226 for tool 114 is mounted to table 202 at a first base position 226a. Tool support structure 226 is optionally mounted to table 202 at a second base position 226b, which again illustrates that the tool support structure may be placed at various positions and orientations for and during teleoperation (e.g. during telesurgery in surgical examples). In FIG. 5D both the position and orientation of the tool support structure's base was shown changed, and in FIG. 5E only the position of the tool support structure's base is shown changed, since the base orientation does not change as it is at various positions along the table rail. But, the tool support structure base position and orientation may change in other configurations, such as when the tool support structure is moved from one side of the table to the opposite side of the table. In addition, the table pose may change, which correspondingly changes the base orientation and position. Again, as discussed above, various combinations of camera and tool support structures are possible. And again, for all these optional combinations, the support structure that supports the camera is either completely physically separate from the support structure that holds the tool that requires registration in the camera's FOV reference frame, or is mechanically coupled via a shared support structure that also holds the tool but without shared kinematic information and is therefore effectively kinematically separate.

2. Alignment for Control

In order to effectively move the distal end of the tool in relation to the camera FOV reference frame, an alignment relationship is determined between the camera FOV and the end effector of the tool—that is, between the reference frame associated with the camera FOV and the reference frame associated with the end effector. In addition, an alignment relationship is determined between the master device and the display that outputs an image from the camera that shows the end effector—between the frame associated with the master control and the frame associated with the display. An example of establishing such an alignment relationship and forcing a master device to a pose that corresponds to a displayed end effector pose is found U.S. Pat. No. 6,424,885 B1 and in U.S. Pat. No. 6,459,926 (filed Sep. 17, 1999), the disclosure of which is incorporated by reference in its entirety. In these examples, a master device is mounted at the end of a robotic master manipulator arm. To establish the necessary master/slave control relationship, the master manipulator arm moves the master device to a pose in the display reference frame that corresponds to the pose of the slave end effector in the camera FOV reference frame. This movement aligns the master device pose with the displayed end effector pose, and so a visually and proprioceptively intuitive control relationship between the master device and the end effector is established. Thus, in various embodiments, the relationships between the end effector reference frame and the FOV reference frame, and between the display reference frame and the master device reference frame, are determined.

In implementations, a user's perception of intuitive master/slave control depends on at least two major perceived correlations between master and slave. First, it depends on the user's perception of the correlation between the master's (the master device) orientation in space and the slave's (end effector) orientation in space—perceived orientation correlation. Second, it depends on the user's perception of the correlation of the master's (master device) direction of movement with the slave's (end effector) direction of movement—perceived direction of movement correlation.

Therefore, the user's proprioceptive sense of the master device's orientation should be within an acceptable tolerance of the user's visual sense of the corresponding end effector image's orientation in the display. For many tools and/or master devices, the long axis of the master device should be perceived as oriented in the direction of the long axis of the end effector in the display. For other tools and/or master devices, however, the master device and/or end effector orientation axes used for control may be other than the long axis. As an example, a pistol grip style master device may not have a long axis perceived as aligned with an end effector's long axis, but the user still perceives an orientation correlation between the pistol grip master and the end effector. Further, if the end effector has a grip function that intuitively corresponds to a master device's grip motion, the orientation of the plane of the master device's grip motion should be perceived as corresponding to the orientation of the plane of the end effector's grip motion in the display. (This is a match between the master device's roll angle around its actual or perceived long axis and the end effector's roll angle around the end effector's long axis.)

Likewise, the user's proprioceptive sense of the master device's direction of movement should be within an acceptable tolerance of the user's visual sense of the corresponding end effector image's direction of movement.

Individual users will have different personal tolerances for perceived orientation and direction of movement correlations. For example, some users may tolerate a perceived orientation correlation mismatch of 20-40 degrees. And, some users are affected by a perceived direction of motion correlation mismatch as low as 5 degrees. We have found that when a telesurgical system first establishes a control relationship between master device and end effector to begin master/slave operation, and as the system continues to update and maintain the control relationship between master device and end effector during master/slave operation, the perceived master/slave orientation and direction of movement correlations are more important than the perceived position correlation for adequate performance.

Figure 5F:
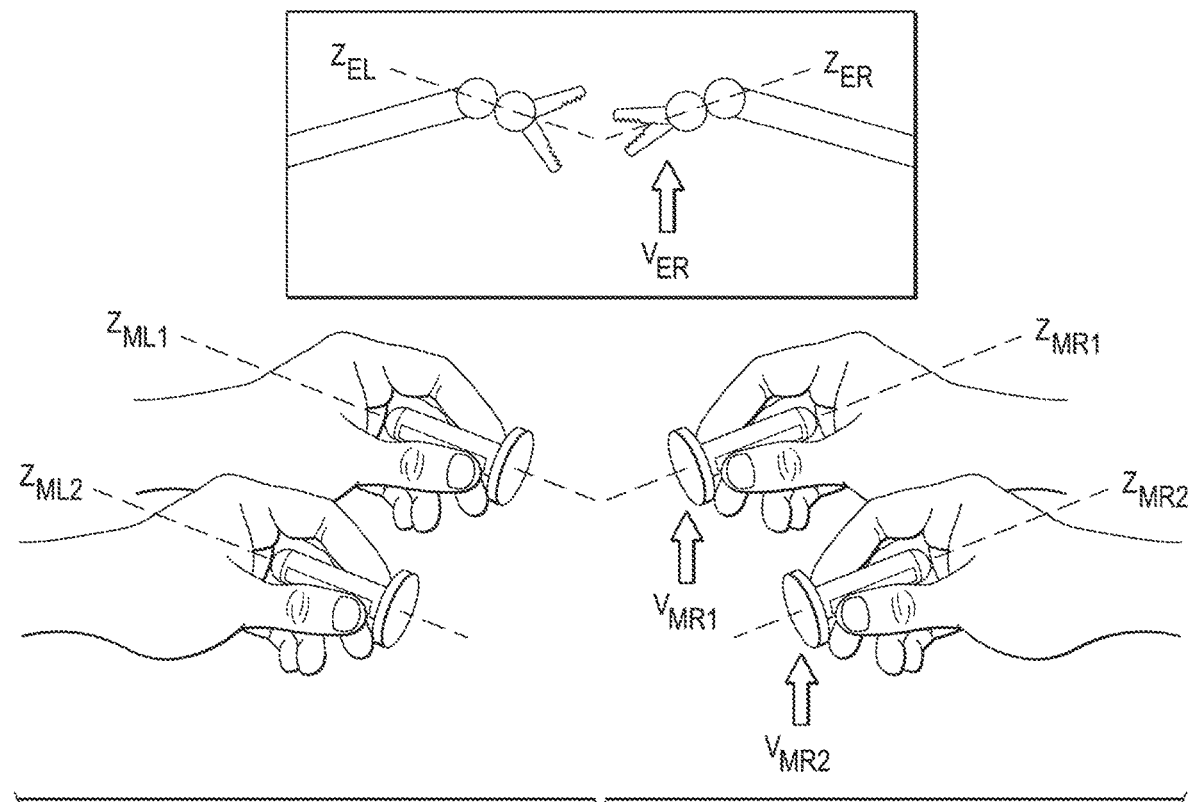

Referring to FIG. 5F, an orientation alignment axis $Z_{EL}$ is associated with the displayed image of the left end effector, and an orientation alignment axis $Z_{ER}$ is associated with the displayed image of the right end effector. Likewise, an orientation alignment axis $Z_{ML}$ is associated with the left master device, and an orientation alignment axis $Z_{MR}$ is associated with the right master device. The master devices with their orientation axes at $Z_{ML1}$ and $Z_{MR1}$ are at positions spaced apart in a way generally corresponding to the way the end effector orientation axes $Z_{EL}$ and $Z_{ER}$ are spaced apart.

The master device orientation axes $Z_{ML2}$ and $Z_{MR2}$, however, are spaced apart farther than the way the end effector orientation axes $Z_{EL}$ and $Z_{ER}$ are spaced apart. Nevertheless, the positions of master device orientation axes $Z_{ML2}$ and $Z_{MR2}$ provide effective intuitive control. In a similar way, differences in vertical (e.g., left higher than right) or depth (e.g., left farther away than right) positions of master device orientation axes $Z_{ML2}$ and $Z_{MR2}$ also provide effective intuitive control. For example, effective control can be established and maintained with the position of the right master device orientation axes at $Z_{ML1}$ and the left master device orientation axis at $Z_{MR2}$.

Still referring to FIG. 5F, a 3D spatial movement $V_{MR1}$ is associated with the right master device at the first master device position, and a parallel 3D spatial movement $V_{MR2}$ is associated with the right master device at the second master device position. Both of these movements $V_{MR1}$ and $V_{MR2}$ are perceived as correlated to the right end effector's 3D spatial movement $V_{ER}$ for effective intuitive control, despite the right master device being at positions spaced apart in 3D space.

3. Orientation Alignment and Orientation-Only Alignment

In order to provide the required perceived correlation in orientation and direction of movement between master device and end effector for the user's effective intuitive control, the control system determines and aligns the relationships between associated frames, both to begin master/slave control for teleoperation (e.g. for telesurgery in surgical examples) and to maintain and update master/slave control during teleoperation (e.g. for telesurgery in surgical examples).

In accordance with an inventive aspect, the required alignment relationships between the camera FOV and the end effector, and between the master device and the display are established with reference to only the orientations of these objects and not with reference to their positions—that is, with reference to the orientations of the reference frames associated with these objects and not with reference to the positions of the reference frames associated with these objects. For control, absolute orientation is determined between an end effector alignment orientation axis and a camera FOV alignment orientation axis, and absolute orientation is established between a master device alignment orientation axis and a display alignment orientation axis. When the orientation relationships are determined for control, the end effector may be located within or outside the camera FOV.

In accordance with an inventive aspect, the required alignment relationships between the camera FOV and the end effector, and between the master device and the display, are established with reference to the full orientations of these objects but with reference to less than their full positions. The full orientation is also called "complete orientation", and the full position is also called "complete position". Examples of less than full position information include no position information, and partial position information such as position information along only one or two axes. Thus, in an example utilizing Cartesian coordinates, the required alignment are established with reference to the orientations of the reference frames associated with these objects around all three Cartesian axes (e.g. rotation around the X, Y, and Z axes), and with reference to the positions of the reference frames associated with these objects along zero, one, or two Cartesian axes (e.g. along none of the X, Y, or Z axes, or along only one or two of the X, Y, and Z axes). Control is then established by using the full orientation information and less than the full position information.

The following description concentrates on using orientation information, and it should be understood that in addition, less than full position information (i.e., along zero, one, or two Cartesian axes) may be optionally combined with full orientation information to establish and maintain control as described.

A full homogeneous transformation may be used but is not necessary to establish and maintain effective alignment between reference frames for intuitive control. Once the orientation of any individual link in the kinematic chain for these objects (which may be the object itself) is known, an effective control relationship can be established with less than full position information for that individual link. Less than full position information for a link may mean no position information for that link, and some embodiments use only orientation information for establishing the control relationship. Using only orientation for alignment simplifies the alignment task because it eliminates the need either to determine the absolute or relative position of these objects or of their support structures, or to construct combined support structures that establish a common reference frame for these objects or support structures. Less than full position information may also mean partial position information, and some embodiments use orientation information and partial position information in establishing the control relationship. Using partial but not full position information also simplifies the alignment task by reducing the amount of position information that is determined. Thus, various separate individual objects and their support structures, as illustrated in FIGS. 5B-5E, may be properly aligned for control. The required alignment relationships to establish effective control are carried out by well-known kinematic transforms from one reference frame to another reference frame.

Once the initial orientation alignment relationships (e.g. orientation-only alignment relationships, or complete-orientation-with-partial-position alignment relationships) required for effective teleoperation control are established among the various reference frames, then changes in both position and orientation with respect to these reference frames are used to carry out teleoperation (e.g. telesurgery in surgical examples). For example, a change in position of a master device is carried out as a corresponding 1:1 or scaled change in position of a tool's end effector, a change in orientation of a master device is carried out as a corresponding change in and orientation of a tool's end effector, and a change in pose of a master device is carried out as a corresponding change in pose of a tool's end effector. But while these control relationships function during teleoperation, the alignments between the frames may be maintained by using only the orientations of the frames and not with reference to their positions, or by using the orientations with reference to less than their full position information.

In one aspect, the end effector orientation is determined in relation to the tool's shaft orientation in accordance with the wrist function. In some instances, all three end effector orientation DOFs with respect to the shaft are independent of the shaft to which the end effector is coupled. In other instances, fewer than the three end effector orientation DOFs with respect to the shaft are independent of the shaft. For example, the end effector pitch and yaw DOFs may be independent of the shaft, and end effector roll orientation around the z-axis is determined by a shaft roll DOF. As another example, the end effector yaw DOF may be independent of the shaft, but end effector pitch and roll is determined by corresponding shaft pitch and roll DOFs. Thus in some instances in which a transform from a tool reference frame to an end effector reference frame occurs to establish the alignment required for control, three, two, or one rotation may be required, depending on the tool's distal end configuration.

In one aspect, the orientation of the end effector reference frame is determined in relation to a reference frame other than the tool's reference frame. For example, as described in more detail below, the orientation of the end effector reference frame is determined with reference to the orientation of a reference frame of a field of view (FOV). For example, in an endoscopic surgery example, the orientation of the end effector reference frame (for a tool in the surgical site) is determined relative to the orientation of a field of view reference frame (for an endoscopic camera having a FOV covering the surgical site in part or whole, also called a camera FOV). In this example, the end effector may be located inside or outside of the field of view associated with the field-of-view reference frame.

In one aspect, the orientation of the input device frame is determined in relation to a reference frame of an image displayed by a display, and viewable by a user interacting with the input device.

In accordance with another inventive aspect, the initial orientation alignment relationship (e.g. orientation-only alignment relationship, or complete-orientation-with-partial-position alignment relationships) required for control is established when an event in the teleoperated system occurs, such as the teleoperated system's computer receiving a signal that indicates the user wishes to begin teleoperation control. Such an event may be a button press or other actively controlled event so that teleoperation is not begun by mistake.

Figure 5G:
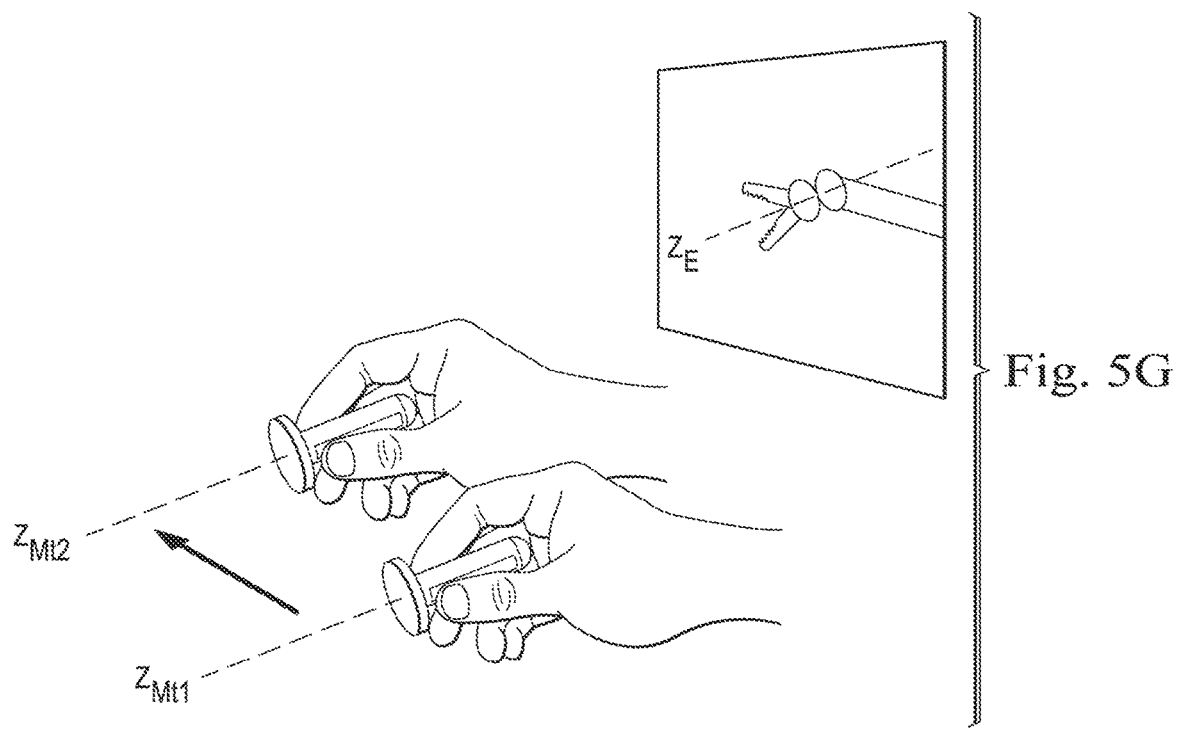

Examples of such system events may be at a transition between teleoperation of one or more tools and teleoperation of one or more endoscopic cameras, exchanging a first tool for a second tool on a teleoperated manipulator, and other actions that are expected to occur throughout a procedure (e.g. through a surgical procedure in surgical examples). As a specific example, one event that optionally may be used to trigger the request to establish the control relationship is an exit from a "clutch" mode in which the master/slave relation between the master control device and the end effector is temporarily suspended. The clutch mode is analogous to the use of a mechanical clutch that engages and disengages a coupling between objects. As shown in FIG. 5G, at a first time t1 a master device orientation axis ZM is at a first position as shown and is perceived as correlated in orientation and direction of movement with the orientation axis ZE of the image of the corresponding slave end effector. That is, the user teleoperates the end effector and senses that the z-axis ZM of master device at time t1 is aligned with the z-axis ZE of the image of the end effector as shown. The user then enters the clutch mode, moves master device to a second position as shown by the arrow, and exits the clutch mode at time t2. At t2 the user again perceives that the orientation axis ZM of master device correlated in orientation and direction of movement with the orientation axis ZE of the image of the end effector as shown, although at t2 the orientation axis ZM is at a different position that at t1.

In accordance with another inventive aspect, the initial orientation alignment relationship (e.g. orientation-only alignment relationship, or complete-orientation-with-partial-position alignment relationships) required to establish control is updated during teleoperation to further refine the relationship, to correct for possible drift in various sensors and other system components, etc. These updates are optionally carried out using only orientation information and not position information. Updates may optionally occur at various times, such as at a predetermined time interval or at one or more system events. As an example of an update at a predetermined time interval, end effector pose is updated approximately every 1 ms (millisecond) to correspond to the master pose, and so the alignment relationship is updated each 100 cycles (approximately every 100 ms). Further, updates may be made at a combination of system events and predetermined time intervals, such when teleoperation is reestablished after a master device clutch movement, and then at a predetermined number of clock cycles after that.

As an alternative, the alignment relationship between frames may be refined by a ratcheting procedure, for example as described in U.S. Pat. No. 8,423,186 B2 (filed Jun. 30, 2009), which is incorporated herein by reference, to converge on master device and end effector perceived alignment in orientation after an event such as clutching. For example, where the orientation of the input-device reference frame relative to the display frame is a first relative orientation and the orientation of the end-effector reference frame relative to the field-of-view reference frame is a second relative orientation, and the first relative orientation differs from the second relative orientation by a difference, the system can update the second alignment relationship multiple times to gradually reduce the difference.

As another example, the system can integrate the orientation difference, and apply a portion of the integrated difference to commanded motion. In this alternative, the end-effector reference frame changes with commanded motion, and the commanded motion dynamically reduces the orientation difference. In an implementation, the system determines: a commanded change in orientation of the end effector, a residual orientation difference, a maximum reduction of the difference (such as a percentage of commanded change in orientation that still maintains orientation intuitiveness, in some cases being limited to a maximum of +/−20% of commanded motion). Then, the system modifies the commanded motion by adding an amount based on the residual orientation difference (such as the residual orientation difference scaled by a scale factor). Such a scale factor can be limited by a maximum scale factor.

In accordance with another inventive aspect where only orientation is used in the alignment relationship, the orientations of various objects and links in kinematic chains may be determined in various ways, as illustrated below. And, even though position information for these objects and links may also be determined, in these aspects it is the orientation information alone that is used to initially establish the alignment relationship required for control, and then to maintain and update the alignment relationship.

Figure 5H:
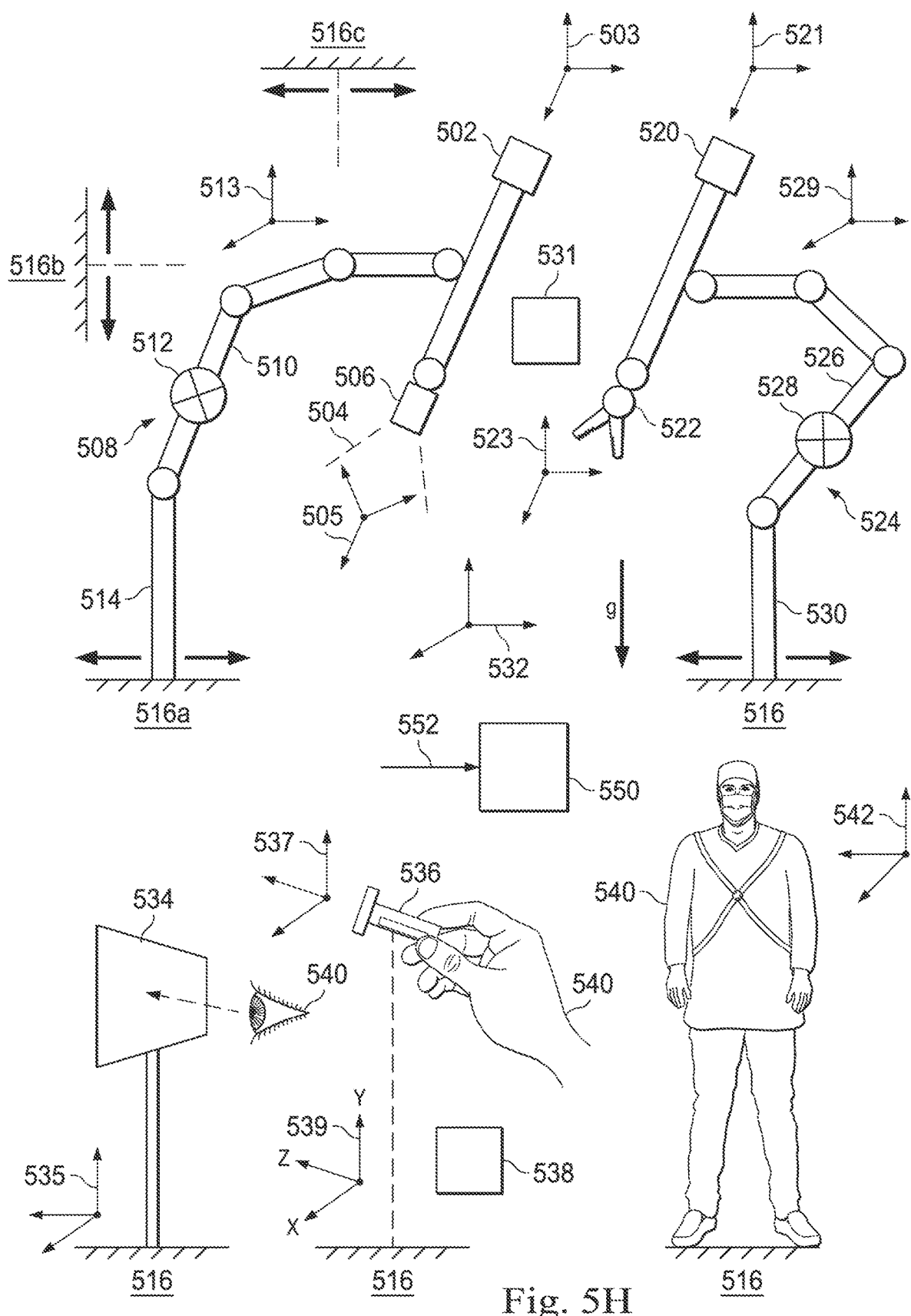

FIG. 5H is a schematic view of teleoperated (e.g. telesurgical in surgical examples) system components and reference frames associated with these components. Where applicable, components are analogous to components illustrated in FIGS. 5A-5F. As shown, camera tool 502 (also "camera 502") has an associated camera tool reference frame 503. Camera tool 502 has an FOV 504 (2D or 3D), which has an associated FOV reference frame 505. If the distal objective end 506 of camera tool 502 is not steerable with reference to the body of the camera tool, then camera tool reference frame 503 and FOV reference frame 505 may be combined.

Camera support structure 508 supports camera tool 502 at a distal end. In some implementations camera support structure has a single link, and in other implementations it has two or more links with each pair of links coupled by a joint. As shown, one link of camera support structure 508 is identified as a camera support target link 510, and a dedicated spatial indicator target 512 is optionally fixed to target link 510. Camera tool support structure reference frame 513 is associated with target link 510 or target 512 as appropriate. Camera support structure 508 further includes a proximal base link 514 at a mechanical ground 516 (e.g., coupled to floor 516a, to wall 516b, to ceiling 516c, or to a structure itself at a mechanical ground, such as a table (fixed or movable) or movable cart). Base link 514 is optionally movable with reference to ground, as indicated by the directional arrows, but is otherwise in a fixed relationship to ground during initial alignment and operation. In some optional implementations, camera support structure 508 is omitted and camera 502 is supported by a person during a procedure. In such an optional implementation, target 512 is optionally fixed to camera tool 502, and camera tool reference frame 503 and camera tool support structure reference frame 513 are combined.

Tool 520 has an associated tool reference frame 521. Tool 520 has a distal end effector 522, which if applicable has an associated end effector reference frame 523 because it is movable with respect to the body of tool 520.

Tool support structure 524 supports tool 520 at a distal end. In some implementations tool support structure has a single link, and in other implementations it has two or more links with each pair of links coupled by a movable joint. As shown, one link of tool support structure 524 is identified as a tool support target link 526, and a dedicated target 528 is optionally fixed to target link 526. Tool support structure reference frame 529 is associated with target link 526 or target 528 as appropriate. Tool support structure 524 further includes a proximal base link 530 at mechanical ground 516 (e.g., coupled to floor 516a, to wall 516b, to ceiling 516c, or to a structure itself at a mechanical ground, such as a table (fixed or movable) or cart). Base link 530 is optionally movable with reference to ground, but it is otherwise in a fixed relationship to ground during alignment and operation.

Spatial orientation determining unit 531 determines the orientations of camera support target link 510, camera support spatial indicator target 512, tool support spatial indicator target link 526, camera support spatial indicator target 528, and camera 502, or a subset of these depending on how the orientations are determined, as required for the system configuration. Orientation determining unit 531 optionally uses any of various known ways to determine the orientation, such as kinematics, electromagnetic localization and other RF-based methods, ultrasonic or acoustic localization, optical tracking based on dedicated targets or natural features, and optical fiber shape sensors. Details are described below. Orientation determining unit 531 is optionally centralized at a single location or distributed at two or more locations, may be optionally integrated into one or more teleoperated system units and support structures, and may be optionally worn by the user.

In some implementations where only orientation information is used for an alignment relationship, the system is configured to sense only orientation information for such alignment relationship. For example, a kinematic support structure is instrumented to only sense joint orientation. Omitting sensors simplifies the design and saves cost. Therefore, in some optional implementations two mechanically-connected support structures are instrumented to sense only orientation and not position. For example, in a kinematic chain support structure for a tool manipulator or a master device, rotational sensors are used to sense rotational joint angles, but position sensors to sense prismatic joint positions are omitted. Likewise, for ungrounded devices, optionally only orientation and not position is sensed, since only orientation may be used to establish and maintain the intuitive control relationship between master and slave devices. In some other implementations that use only orientation information for an alignment relationship, position information is partially or fully sensed.

Also shown is an optional world reference frame 532 and gravity vector (g), which may be used to define or determine one or more of the reference frames or to sense a change in orientations of one or more of the reference frames. World reference frame 532 is optionally used for the kinematic transformations between the various system component reference frames.

FIG. 5H further shows a display 534 on which images from camera tool 502 are displayed. Display reference frame 535 is associated with display 534. Display 534 is supported with reference to ground 516. When the distal end of tool 520 is in FOV 504, a corresponding image is displayed on display 534 and is viewed by the user 540 (e.g. a surgeon or skilled clinician or other personnel in medical examples).

The user 540 holds master device 536, which has an associated master device reference frame 537. Master device 536 is optionally mechanically grounded or ungrounded, as symbolized by the dashed line to ground 516. Whether grounded or ungrounded, the orientation of master device 536—the orientation of master device reference frame 537—is sensed and determined by master orientation determining unit 538, which optionally uses any of various known ways to determine the orientation, such as kinematics, optical tracking, or other wireless tracking (e.g., technology supplied by Leap Motion, Inc., San Francisco, California, U.S.A.). For control purposes, an orientation of master device reference frame 537 may be determined with reference to a reference frame on a kinematic support structure (if applicable) or with reference a fixed reference frame, such as master orientation unit reference frame 539 or world reference frame 532.

FIG. 5H also shows the user 540 oriented (standing, seated) to ground 516. An optional user reference frame 542 is associated with user 540. User reference frame 542 is a body-centric reference frame defined with reference to a point on the user's body (e.g., the eye, another position on the body, clothes or equipment the user is wearing, etc.).

A centralized or distributed computer control system 550 receives information about the orientations of the various teleoperated system components and performs the rotational transforms necessary to establish the initial alignment relationships required for effective teleoperation control and maintain the alignment relationships as required. When the alignment relationships are established and any other conditions necessary for entering a master/slave control mode are met, computer control system 550 outputs a command to operate in the teleoperated system in the master/slave control mode. Examples of optional required conditions to enter the master/slave control mode are a determination that the end effector is in the camera FOV, a determination that the user is looking at the display (see e.g., U.S. Provisional Patent Application No. 62/467,506 (filed Mar. 6, 2017), which is incorporated herein by reference), and other safety-related conditions.

In general, computer control system 550 establishes the required initial orientation alignment relationships to enter the master/slave following mode between master device 536 and surgical tool 520. Relative orientation transform relationships are established between the end effector frame and the FOV frame and between the master device frame and the display frame. A direct transform relationship between master device frame and end effector frame is not required. As described above, the transform relationships for the initial alignment do not account for position information of the end effector or master device. The chain of transforms varies depending on the system architecture and the various reference frames that may apply to the components in the system architecture. In some embodiments, the required initial orientation alignment relationship is an orientation-only alignment relationship, and the associated transform relationship is an orientation-only transform relationship that transforms only the orientation. In some embodiments, the required initial orientation alignment relationship is a complete-orientation-with-partial-position alignment relationship, and the associated transform relationship is a complete-orientation-with-partial-position transform relationship that transforms position only partially, such as only along one or two axes in a three-dimensional space.

For example, with reference to FIG. 5H, a transform relationship from master device reference frame 537 to end effector reference frame 523 may include a transform from master device reference frame 537, to master orientation unit reference frame 539, to tool support structure reference frame 529, to tool reference frame 521, to end effector reference frame 523. Optionally a transform to and from world reference frame 532 is included, generally between reference frames associated with a control unit and a patient-side unit.

In addition, computer control system 550 establishes an initial orientation transform relationship between master device reference frame 537 and display reference frame 535. In some embodiments, the initial orientation transform relationship is an orientation-only transform relationship. In some embodiments, the initial orientation transform relationship is a complete-orientation-with-partial-position transform relationship.

When establishing the initial master/slave relationship between master device and end effector, the reference frame transform chain between master device and end effector is established for the master device for any master device position and orientation in space at which the user is holding the master device. The user may choose to visually align the positions and orientations of the master device and the displayed end effector images, but the user is not required to do so in order to establish the control alignment. That is, the user may choose to hold the master device without visually aligning the positions and orientations of the master device and the displayed end effector image. For example, the user may hold the master device at the chest or abdominal level, out of the user's field of view, optionally placing the forearm on an armrest for stability and fatigue reduction. As another example, the user may be oriented at an oblique angle away from the display while holding the master device when initial control alignment is established. For example, a user's shoulders may be turned 45 degrees from the display so that the user can operate a master device in one hand and a manual tool (e.g. a laparoscopic tool in surgical examples) in the other hand.

In an aspect of establishing the master/slave relationship between master device and end effector, master/slave teleoperation is optionally allowed on the condition that the master device is within a certain orientation tolerance. The tolerance may be based on the master device's orientation within the master orientation unit reference frame (FIG. 5H, element 539). Or, the tolerance may be based on the master device's orientation within the display reference frame (FIG. 5H, element 535), which in effect bases the tolerance on based on the orientation of the displayed image of the end effector. Or, the tolerance may be based on the master device's orientation within some other reference frame. The orientation tolerance may apply to one (e.g., roll), two (e.g., pitch and yaw), or all three rotations in Cartesian space. And, orientation tolerances for each of these rotations may be different. For example, if the master device includes a grip DOF within a plane, then the roll tolerance with reference to the end effector's corresponding grip DOF plane may be smaller (e.g., ±10°) or larger (e.g., ±20°) than the pitch or yaw tolerances (e.g., ±15°) with reference to the end effector's pitch and yaw.

Figure 5I:
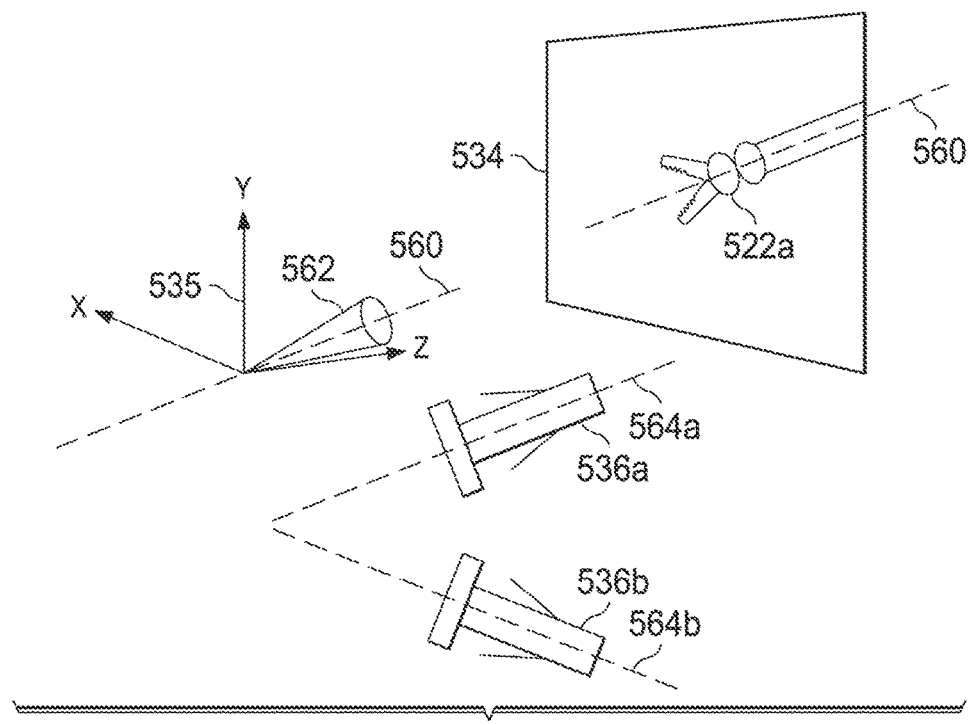

FIG. 5I is a diagrammatic view that illustrates the requirement for the master device orientation to be within a certain tolerance of the displayed end effector orientation in order to establish alignment for control. As depicted, an image 522a of end effector 522 is shown on display 534. From the established kinematic relationship between FOV reference frame 505 and end effector reference frame 523, an orientation 560 of the end effector image 522a in display reference frame 535 is determined. (For clarity, reference number 560 is shown twice in the figure-once in relation to the display, and once in relation to the display reference frame.) Then, an alignment tolerance 562 is determined with reference to the orientation 560. In FIG. 5I this tolerance is illustrated by a circular cone having orientation 560 as its central axis. Other alignment tolerance shapes may optionally be used, such as elliptical cones, pyramids, and similar shapes that can be defined with reference to the orientation axis.

The kinematic relationship between the display reference frame and the master device reference frame is determined. Then as a first example, as shown in FIG. 5I master device 536a is determined to have an orientation 564a. Orientation 564a is determined to be within alignment tolerance 562, and so master/slave control between master device 536a and end effector 522 is permitted. As a second example, master device 536b is determined to have an orientation 564b. Orientation 564b is not within alignment tolerance 562, and so master/slave control between master device 536b and end effector 522 is not permitted until orientation 564b is determined to be within alignment tolerance 562. In some instances the control alignment is automatically established as soon as the master device orientation is within the alignment tolerance, and optionally a visual, audio, haptic, or similar indication is output to the user as a signal that the master/slave control relationship is in effect. A ratcheting function as described above may be used. For the required control relationship to be established in other instances, in addition to the master orientation being within the alignment tolerance, the system must receive another event, such as a button press, verbal command, or similar input that requests the control relationship be established. This approach to establish a master device orientation tolerance in order to begin master/slave control applies to situations in which the tolerance is based on other reference frames.

In some instances in which a master control is at the distal end of a robotic arm, the control system 550 optionally commands the robotic arm to orient the master device's orientation alignment axis with reference to the master orientation unit reference frame (FIG. 5H, element 539), or the display reference frame (FIG. 5H, element 535), or some other reference frame. For example, control system 550 may command the arm to place the master device at an aligned orientation with reference to the displayed end effector image, and it commands the arm to place the master device at a defined default position with reference to the display, or at the current position with reference to the display, instead of at a position corresponding to the displayed image of the end effector.

If two master devices are used to control a single object, the perceived orientation and direction of movement correlations between the master devices and the object may be perceived orientation and direction of movement correlations between the master devices acting together and the object. An example might be the two master devices acting as a handle bar with a straight connecting axis between them. As the master devices are moved together to change the position of the connecting axis, the position of the object correspondingly moves (e.g., a camera FOV moves up-down, left-right, in-out). As the master devices are moved together to change the orientation of the connecting axis, the orientation of the object correspondingly changes (e.g., a camera FOV tilts up-down, pans left-right, rolls clockwise-counterclockwise). Here again only orientation information need be used, and position information is not required. For example, the masters may be spaced close together or far apart on the connecting axis, and the spacing on the connecting axis may change as the object is controlled (e.g., farther apart provides finer orientation control; closer together provides increase range of motion).

Figure 5J:
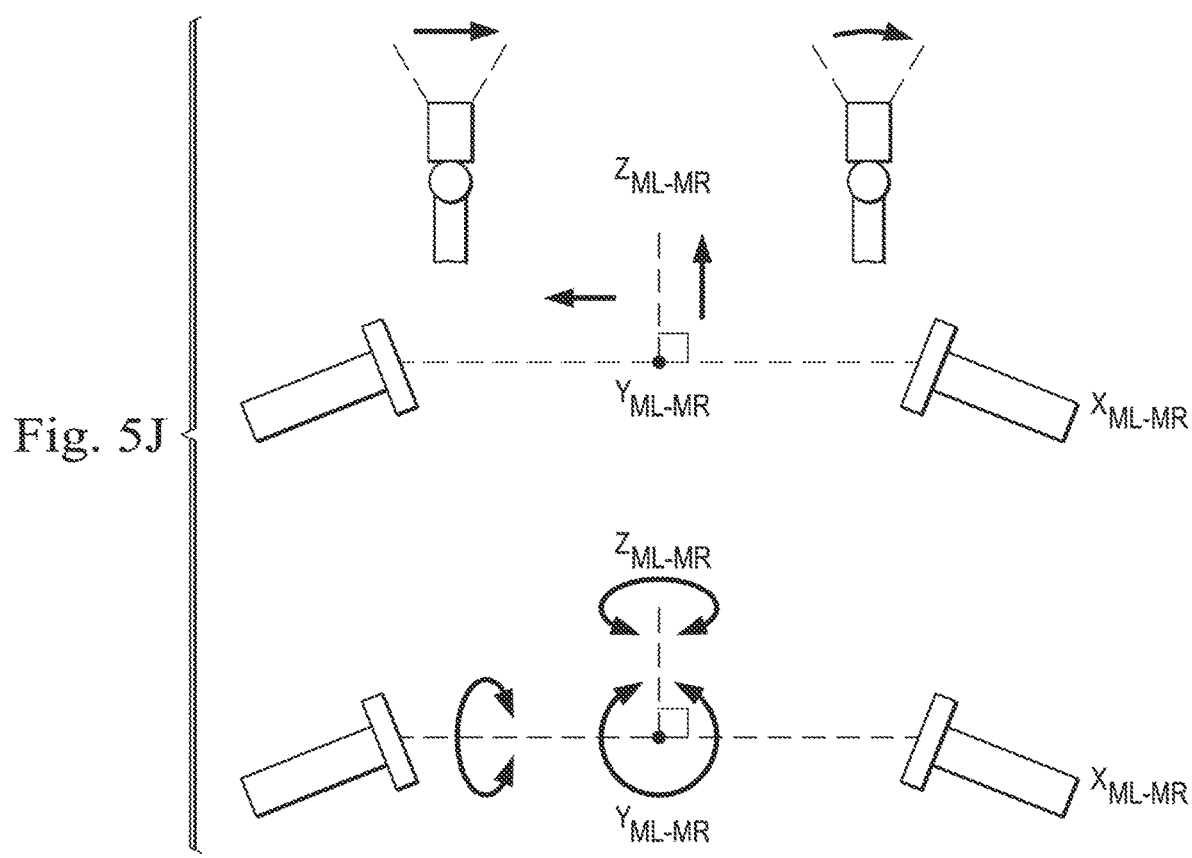

As shown in FIG. 5J, for example, a connecting axis $X_{ML-MR}$ is defined between left and right master devices. A normal axis $Z_{ML-MR}$ may also be defined for control. As axis $X_{ML-MR}$ is moved to the left, a camera is either translated or rotated to move correspondingly, optionally either giving the user the sensation of moving the scene to the right (FOV moves right as shown) or the camera to the left (FOV moves left). The camera may translate or rotate as shown. Insertion and withdrawal is controlled by movements along axis $Z_{ML-MR}$. Changes in elevation along another mutually orthogonal axis $Y_{ML-MR}$ may also be done. Similarly, the FOV position or orientation may be controlled by rolling around the connecting axis and its Cartesian orthogonals (e.g., FOV tilt by roll around $X_{ML-MR}$, FOV pan by roll around $Y_{ML-MR}$, and FOV roll by roll around $Z_{ML-MR}$). Approaches similar to ones used to establish initial alignment relationships may be used to maintain alignment relationships during teleoperation as described herein.

4. Determining Spatial Relationships

As discussed above, the operational environment of a teleoperated system may include two or more manipulators for various tool and camera combinations. For example, the patient-side environment of a telesurgical system may include two or more manipulators for various surgical tool and endoscopic camera combinations. And, one or more of these manipulators may not have a predetermined fixed spatial relationship with respect to the other manipulators. Similarly, there may not be a predetermined fixed spatial relationship among the one or more master devices and the display screen. In this situation, it is not possible to establish and maintain the control relationship necessary for teleoperation based only on sensing the angular relation between the various kinematic pairs (e.g., by using joint angle or similar sensors) and kinematic transformations for each individual unit. The spatial relationships between units are determined in order to establish and maintain effective intuitive control.

Figure 6A:
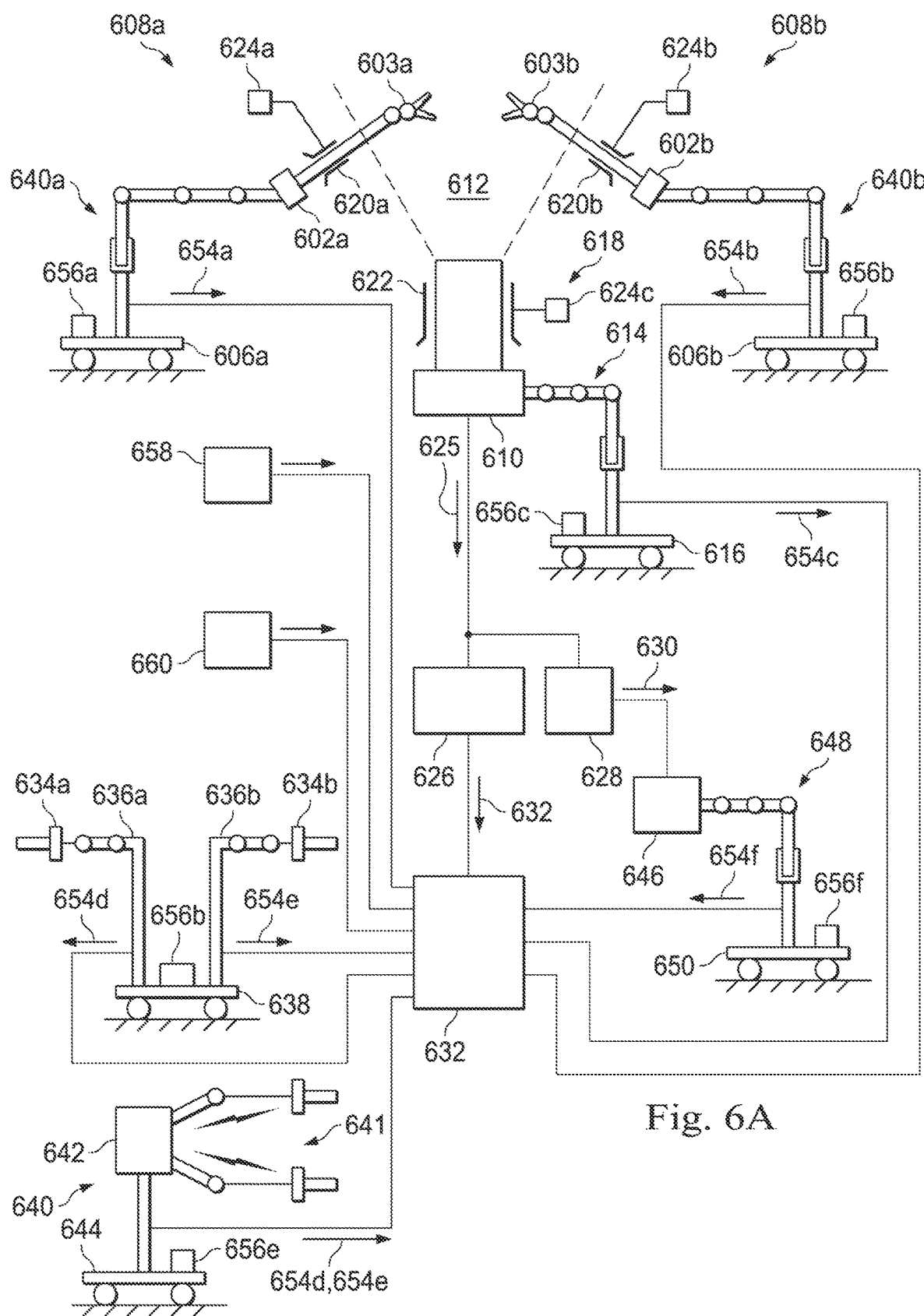
FIG. 6A is a schematic view that illustrates various spatial determination methods in a teleoperated system.

FIG. 6A is a schematic view of a teleoperated system (specifically a telesurgical system is shown) that incorporates inventive aspects of determining spatial relationships. For simplicity, several aspects are illustrated as incorporated into FIG. 6A, and various optional telesurgical system configurations are described further below. Not all depicted and described aspects are required in a single embodiment. Objects depicted in FIG. 6A are analogous to objects depicted in FIGS. 5A-5J, as applicable (e.g., tools, endoscopic camera, support structures, control system, spatial sensors, movable units, etc.).

As shown, there are two teleoperated surgical tools 602a, 602b, each with a corresponding end effector 603a, 603b. Each tool 602a, 602b is actuated by a corresponding manipulator 604a, 604b, each mounted on a corresponding base 606a, 606b to make up a corresponding patient-side unit 608a, 608b. Likewise, an endoscopic camera 610 is shown, and it has a FOV 612. Endoscopic camera 610 is actuated by a corresponding manipulator 614, which is mounted on a base 616, and together they make up a patient-side unit 618. As shown, the patient-side units 608a, 608b, and 618 are movable with respect to one another—there is no mechanical support structure common to any of them that fully constrains their relative spatial relationships. Hence, the patient-side units 608a, 608b, and 618 are generally as described above.

Each surgical tool 602a, 602b enters the body via a corresponding optional cannula 620a, 620b. Likewise, endoscopic camera 610 enters the body via optional cannula 622. The tool end effectors 603a, 603b are positioned within FOV 612. Three optional vibration sensing/injecting units 624a, 624b, and 624c are shown, each attached to a corresponding one of the cannulas 620a, 620b, and 622. Alternatively, vibration sensing/injecting units 624a, 624b, and 624c may be coupled to any position on a patient-side unit or other telesurgical system unit.

Captured image data 625 travels from endoscopic camera 610 to optional machine vision processor 626. Image data 625 also travels to display image processing unit 628, which in turn processes the captured image data and outputs display image data 630 for display. Machine vision processor 626 outputs machine vision spatial data 632 for use as described below.

FIG. 6A also shows master devices 634a, 634b to be operated by a user. Each master device 634a, 634b is supported by a corresponding mechanical support structure 636a, 636b. As shown, support structures 636a, 636b are mechanically coupled in a fixed spatial relationship and are each mounted to a movable common base 638. Optionally, each support structure 636a, 636b is mounted to a separate movable base. Also shown is an optional grounded or ungrounded master control device configuration 640, in which the master device 641 poses are sensed by master device spatial sensing unit 642 (see also FIG. 5H, orientation determining unit 538; FIGS. 5B and 5C, control input receiver 160c). Spatial sensing unit 642 may be fixed in space, or it may optionally be mounted to a movable base 644. Display 646 is optionally mounted at a fixed position, mounted on movable support structure 648, or worn by the user. Support structure 648 may have a base that is fixed in space, or the base may be mounted to a corresponding movable mechanical base 650, or the base may be mounted on a base common to the base corresponding to the master control devices, such as base 638 or base 644. Hence, the components associated with master control devices 634a, 634b and display 646 are generally as described above.

FIG. 6A further shows a control system 652 for the telesurgical system (see also FIG. 5H, control system 550; FIG. 4, computer 113). Control system 652 executes programmed instructions to carry out the alignment and other system control functions as described herein. Control system 652 is in signal communication with patient-side units 608a, 608b, and 618. It is also in signal communication with master devices 634*a*,634*b*. By this signal communication, control system 652 receives spatial information 654*a*,654*b* associated with end effectors 603*a*,603*b*, spatial information 654*c* associated with FOV 612, and spatial information 654*d*,654*e* associated with master devices 634*a*,634*b*. Optionally, control system 652 receives spatial information 654*f* associated with display 646 if it is not mechanically coupled to a master device.

Optional spatial indicators 656*a*-656*f* are mounted to bases 606*a*, 606*b*, 616, 638, 644, and 650. As shown, spatial detecting unit 658 (centralized or distributed sensing) is associated with spatial indicators 656*a*-656*c*, and spatial detecting unit 660 (centralized or distributed sensing) is associated with spatial indicators 656*d*-656*f*. Optionally, however, a single spatial detector unit may be associated with all spatial indicators in a telesurgical system. Referring to FIG. 5H, targets 512,528 and orientation determining unit 531 are examples of spatial indicators and detectors.

Therefore, inventive aspects determine the spatial relationships between telesurgical system units that are not in permanent, fixed mechanical relationships. The relationships are determined in order to establish, achieve, and maintain intuitive motion based on inputs from the user's master control devices, but with acceptable interference, or without interfering, with the operating room environment. For example, the spatial relationship between manipulators for the end effectors and the endoscopic camera, or directly between the end effectors and endoscopic camera themselves, is determined when there is no fixed mechanical relationship between them. The determined relationships are then used to establish the transformations necessary for the teleoperated control relationship. At a minimum, only the orientations are determined. In some implementations, however, some position information may be determined for one or two axes, or full pose information may be determined.

In some aspects the spatial determination methods use external hardware, such as spatial indicators 656*a*-656*f* and spatial detecting units 658,660. But, this external hardware is sized and positioned so that it does not interfere with the operating room environment. In other aspects, the spatial determination methods do not require additional hardware and are contained within a telesurgical system's existing hardware. For example, an additional data processing unit such as a video data processor or machine vision processor may be added inside an existing unit.

Various ways may be used to determine the spatial relationship between telesurgical system units that are movable with reference to one another by localizing the units to a common single reference frame as necessary. The single reference frame may be a world reference frame that is defined apart from the telesurgical system (see e.g., FIG. 5H, frame 532). Or, the single reference frame may be associated with a device in the telesurgical system, such as the base of a teleoperated manipulator unit.

In the disclosure that follows, reference is made to a "reference base" of a unit, which in some implementations is the actual physical base of a unit that rests on the floor or on another supporting structure that is fixed in the world reference frame. But, persons of skill in the art will understand that the "reference base" may be arbitrarily defined at any point on a patient-side unit that remains stationary in a world reference frame during telesurgery. Since each "reference base" is movable, the relationship of the reference base or bases is determined once the reference base is at a pose that will be stationary during telesurgery. Referring to FIG. 6A, bases 606*a*, 606*b*, 616, 638, 644, and 650 are examples of such movable reference bases and will be used as illustrations of reference bases. Operating principles are illustrated in terms of the patient-side units 608*a*, 608*b*, and 618, and these principles apply to user control units as well as applicable for a particular system configuration. Features and functions associated with spatial indicators 656*d*-656*f* and spatial detecting unit 660 are analogous to features and functions for spatial indicators 656*a*-656*c* and spatial detecting unit 658.

One spatial relationship determining method is to establish a temporary, localized, mechanical relationship between a pair of units (e.g., two patient-side manipulator units) by affixing a temporary, kinematically instrumented, direct mechanical coupling (e.g., a jointed linkage with joint angle sensors) between units to determine the spatial relationship. The instrumented coupling allows the kinematic relationship to be determined once the units are posed for telesurgery and reposed during telesurgery. But in some situations such mechanical localization methods are not practical for the operating room. For example, the equipment used for these methods may interfere with sterile drapes and other operating room equipment. Or, sterile drapes and other operating room equipment may interfere with the equipment used for these methods. Further, the equipment used for these methods may consume excessive space in the patient-side environment, may be expensive, and may be difficult to operate because it requires frequent calibration and other maintenance.

Another spatial relationship determining method is to adapt an indoor locator system approach for use with a telesurgical system in the operating room environment. (In this context, the term "locator system" may be configured to provide some or all of the parameters orientation, some or all of the parameters for position, or some or all of the parameters for both orientation and position.) These locating system approaches may find and track actively transmitting objects, or they may find and track an object's ambient presence.

One aspect of a locator system approach is to position one or more sensors on each unit to detect one or more synthetic or natural features on one or more other units. Synthetic features may actively transmit energy (a "beacon"; e.g., infrared or visible light, RFID, ultrasound) or may be passive (e.g., dedicated spatial indicator targets). The one or more sensors are used to determine a spatial relationship between one or more pairs of units, which is then used for teleoperated control as described. In some situations, however, a line-of-sight method is not practical for the operating room because the line-of-sight may be blocked by operating room equipment, sterile drapes, etc. And, if three or more units are involved, multiple lines of sight must be clear between multiple pairs of units. But, in some situations a line of sight will be nearly always be clear, such as between a unit and the operating table (see e.g., U.S. patent application Ser. No. 15/522,180 (filed Apr. 26, 2017; U.S. national stage of International Application No. PCT/US2015/057664) (disclosing "System and Method for Registering to a Surgical Table", which is incorporated herein by reference).

Another aspect of a locator system approach is to place one or more sensors at corresponding fixed positions in the operating room environment at locations which allow lines-of-sight to units (e.g., high on a wall, or on the ceiling) and to track synthetic or natural features on the various movable units. Synthetic features may be beacons or passive as described above. Spatial indicators 656*a*-656*c* also illustrate natural physical features that can be sensed. An advantage of using two or more sensors is that multiple possible lines-of-sight ensure that a unit will always be detected, and multiple lines-of-sight between two or more sensors and a single unit provides redundancy and possible refinement of the determination of the unit's pose.

As an example implementation of this fixed-sensor approach, a single optical sensor is placed at a fixed pose in the operating room environment, and the single optical sensor detects passive dedicated synthetic optical targets or natural features on one or more patient-side units. Spatial indicators 656a-656c in FIG. 6A illustrate such targets or natural features (see also FIG. 5H, targets 512 and 528). A calibration establishes the spatial relationship between the coordinate frame of each target and its corresponding unit base frame. For example, spatial detecting unit 658 acts as an optical tracker, and the spatial relationship between spatial indicators 656a and 656b is determined. Then, forward kinematic transformations are used to determine the pose of each end effector 603a,603b with respect to its corresponding target. Since all target frames can be expressed in a single optical tracker frame as a common base frame, or other designated common frame, the relative transformations between end effector frames can be calculated by using a combination of measured optical tracker data and forward kinematics of the patient-side units 608a, 608b.

As another example implementation of the fixed-sensor approach, two or more optical sensors are placed at fixed poses in the operating room environment, and the optical sensors detect passive dedicated synthetic optical targets or natural features on one or more patient-side units. Control is then established as described above.

As another example implementation of the fixed-sensor approach, one or more RFID or ultrasound beacons are placed on each unit, and one or more sensors are fixed in the operating room environment to detect the beacons. The pose or poses of the one or more units are determined from the sensed beacons, and control is then established as described above.

As another example implementation of the fixed sensor approach, a combination of synthetic and/or natural features is sensed. Such a combined sensor type approach offers robustness and reliability over a single sensor type approach. For example, an explicit target pattern on one patient-side unit and natural features of a second patient-side unit are sensed, or a combination of explicit target patterns and natural features of each patient-side unit are sensed.

A second aspect of a locator system approach is to place one or more sensors on each movable unit and track one or more synthetic or natural features fixed in the operating room environment at locations that are easily sensed by the units (e.g., high on a wall, or on the ceiling). As with the fixed-sensor aspect, in this fixed-feature aspect synthetic features may actively transmit energy (a "beacon"; e.g., light, RF, ultrasound) or may be passive (e.g., dedicated spatial indicator targets). In this fixed feature aspect, spatial indicators 656a-656c in FIG. 6A illustrate such sensors (see also FIG. 5H, elements 512 and 528), and spatial detecting unit 658 illustrates the one or more fixed features in the operating room environment. The control system receives spatial information from the one or more units, and then control is established as described above.

In a manner similar to the fixed-sensor and fixed-feature locator system approaches, another alternative is the use of simultaneous localization and mapping (SLAM) technology tailored for use with a telesurgical system in an operating room environment. Various SLAM methods exist. See e.g., U.S. Pat. No. 9,329,598 B2 (filed Apr. 13, 2015) (disclosing "Simultaneous Localization and Mapping for a Mobile Robot") and U.S. Pat. No. 7,689,321 B2 (filed Feb. 10, 2010) (disclosing "Robust Sensor Fusion for Mapping and Localization in a Simultaneous Localization and Mapping (SLAM) system"), which are incorporated herein by reference. Detection and tracking of moving objects (DATMO) technology may be combined with SLAM. See e.g., U.S. Pat. No. 9,727,786 B2 (filed Nov. 14, 2014) (disclosing "Visual Object Tracking System with Model Validation and Management"), which is incorporated herein by reference. Multiple sensors ensure sufficient coverage and overlapping operating room reconstructions in consideration of other operating room equipment (surgical table, anesthesia station, etc.) and the need to move the patient-side units in relation to such equipment. SLAM and/or DATMO sensors may be fixed in the operating room environment, mounted on movable units, or both. The base frame orientations required for control are determined, and then control is established as described above.

As an alternative to a modified indoor locator system approach, a machine vision approach may be used to track the tools directly in the stereoscopic images captured by the endoscopic camera. The tracking information is used to determine the pose of the end effector(s) directly in the reference frame associated with the camera's field of view. Referring to FIG. 6A, machine vision processor 626 transmits spatial data 632 about the end effector to control system 652. The tracked relationships are used to determine the relative pose of the manipulator bases, which are stationary during telesurgery.

In one implementation, machine vision is in continuous use to track the poses of the end effectors. In an alternate implementation, once the relationship between the manipulator bases has been determined from machine vision and kinematic information, the alignment between the end effectors can be determined based on kinematic information alone, and there is no need for further machine vision tracking. Referring to FIG. 6A, control system 652 receives such kinematic data as spatial information 654a-654c from patient-side units 608a, 608b, and 618. This use of kinematic data reduces the computational load considerably over continuous machine vision tracking. In yet another alternative implementation, machine vision tracking is used at intervals (e.g., every 100 ms, every 1 s, etc.) to update the pose information, and this periodic update implementation is still a considerably smaller computational load over continuous machine vision tracking.

As another alternative, a spatial determining system is based on optical fiber shape sensors integrated with cables associated with each unit. A cable interconnection between units, or between two units and a common node such as the control system unit, includes an optical fiber shape sensor (e.g., one that incorporates fiber Bragg grating technology). The shape sensor technology is used to determine the spatial relationship between the interconnected units. Cables that transmit control or video data may be modified to include optical fiber shape sensors.

The aspects above may be used to determine full pose information (full orientation and position information), or they may be used to determine less than full pose information (e.g., in a three-dimensional Cartesian space, partial orientation information around only one or two Cartesian axes and/or partial position information along only one or two Cartesian axes). As discussed above, in various embodiments including for many manipulator assembly implementations at the patient side, only the relative orientations between the camera and one or more tools is required for effective control alignment relating the tools to the camera.

And so, only the relative orientations between these objects or individual links in kinematic chains that support these objects are required. Likewise, for user control in some embodiments, only the relative orientations between the displayed image of an end effector and a master device are required. Consequently, these aspects can be simplified or made more robust, because they need only estimate half the number of variables (i.e., orientation, and not position). If the need to determine and track full pose information is eliminated, and only orientation information is determined, then additional spatial determination methods are available.

In one alternative orientation determining approach, spatial indicators 656a-656f illustrate a 3-axis accelerometer and a 3-axis magnetometer combination. It will be recalled that the spatial indicators may be located at any link in a movable unit, or on an object itself, such as on an endoscopic camera.

Figure 6B:
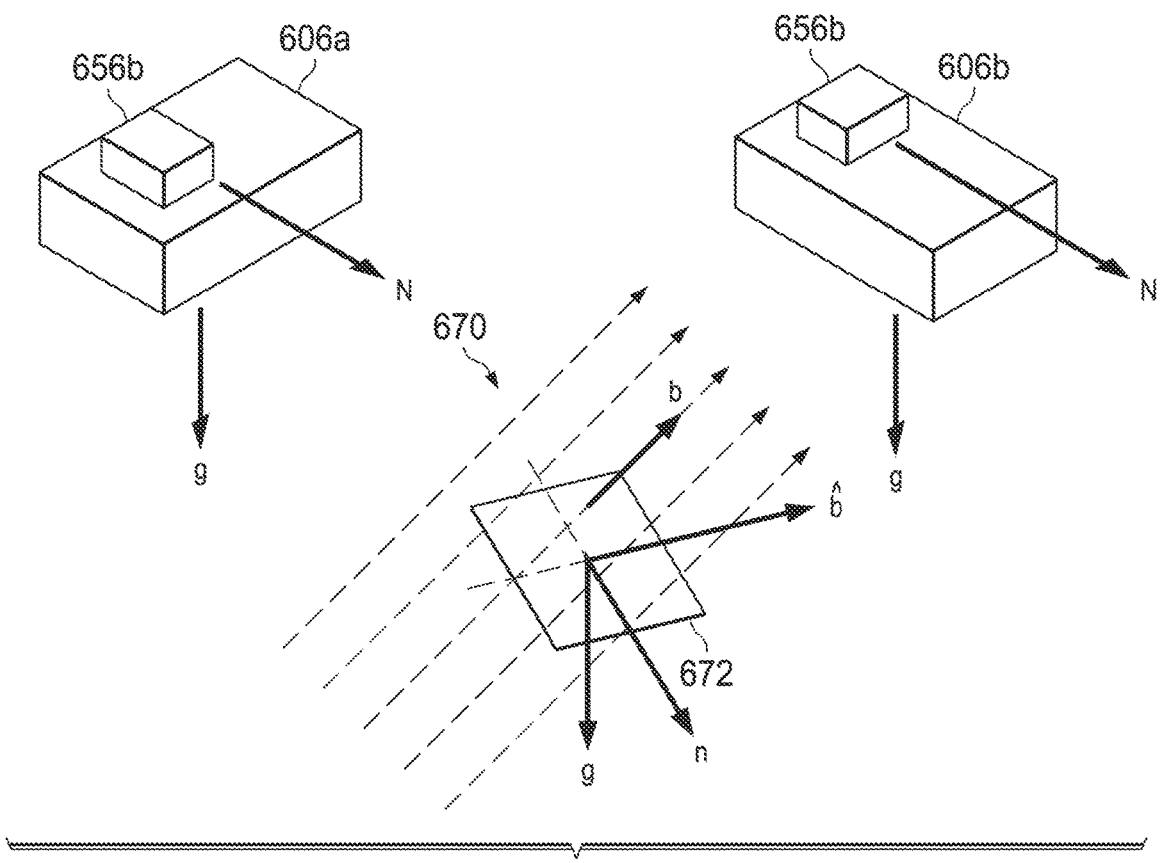
FIGS. 6B-6C are diagrammatic views that illustrate a determination of magnetic bearing.

As shown in FIG. 6B, for example, spatial indicators 656a,656b are each a combination of a 3-axis accelerometer and a 3-axis magnetometer mounted to corresponding bases 606a,606b. The combinations of both spatial indicators 656a,656b each determine gravity vector g and bearing with respect to the earth's magnetic north N, and so they are constant for the two units. As shown, for the local magnetic field 670, b is the local magnetic field vector, g is the gravity vector, and the bearing $\hat{b}$ is the magnetic field projected onto a plane 672 perpendicular to g to indicate magnetic north.

$$n = g \times b$$

$$\hat{b} = n \times g$$

From the magnetic north bearing, the gravity vector bearing, and kinematic information, the spatial orientations of the corresponding bases 606a,606b are determined, and so the relative spatial orientations of the corresponding end effectors 603a,603 are determined for the initial alignment relationship. Likewise for FOV 612 and user control units. Then, once the initial control alignment is established, kinematic information may be used to provide full pose information for master/slave teleoperation.

There may be a magnetic field disturbance in the operating room environment due to local magnetic materials, electric motors, electromagnetic field generators, nearby ferrous materials, etc. In general, the patient-side units should be placed so that the accelerometer/magnetometer combinations are away from these things. If the north bearing errors cause discrepancies in the north bearings for two or more patient-side units that are large enough to cause the initial alignment between the units to affect intuitive master/slave control, however, an alignment correction is necessary. For instance, identical motions of the left and right master input devices may result in different motions of their corresponding end effectors (e.g., the left end effector moves directly left as viewed in the display when the associated left master is moved directly to the left, but the right end effector moves up and to the left as viewed in the display when the associated right master is moved in the same direction directly left).

Figure 6C:
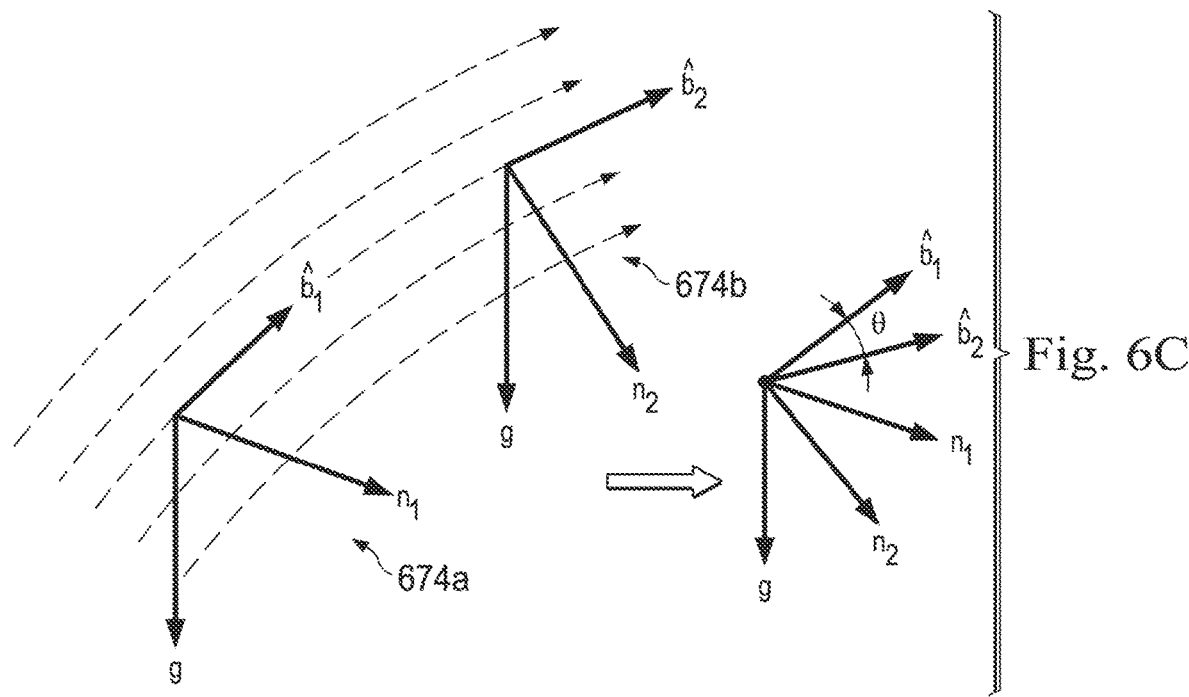

Therefore, an alignment adjustment function is provided, and the user may adjust and fine tune the relation of the image of each tool with respect to the perceived orientation of the corresponding master device. Since the orientation misalignment is due only to different determined north bearings, this adjustment is a one DOF adjustment for each tool with respect to the FOV frame. As shown in FIG. 6C, for example, a first bearing $\widehat{b_1}$ is determined for a first patient-side unit base reference frame 674a, and a second bearing $\widehat{b_2}$ is determined for a second patient-side unit base reference frame 674b. Since the bearings are different, the user may adjust the angle θ as shown between them in order to obtain an alignment for intuitive control. In this way, identical motions of the master input devices (e.g., directly to the left as perceived by the user) will result in identical motions of the corresponding tools (e.g., directly to the left as viewed in the display). This one DOF adjustment is much easier for the user to make as compared to adjusting an entire 3D rotation to make the correction, and it illustrates that this one DOF adjustment approach may be applied to any spatial determining approach for orientation in which one rotational alignment produces a non-intuitive control relationship. This may occur, for example, if a support structure base is moved or if a person holding the endoscopic camera moves.

An alternative way of making the rotational correction is to use external tracking or machine vision approaches as described above to determine the misalignment, and the determined misalignment is used to make the correction. As described above, these correction approaches may be done at intervals to reduce computational load. Further, the combination of the accelerometer/magnetometer approach and a second spatial determining approach offers a more robust and computationally less demanding solution because the second approach is simplified as it determines orientation in a single DOF. For example, an accelerometer/magnetometer approach may be used to provide an initial estimation of a tool end effector orientation in an endoscopic camera field of view, and then by using this initial estimation a machine vision tracking task can be sped up or made computationally less demanding.

As another alternative spatial determining approach, a 3-axis gyroscope is coupled in a fixed position to each unit. Each gyroscope is calibrated to a known orientation, and then the gyroscopes are used to determine subsequent orientations as the units are moved. Calibration may be accomplished in various ways, such as a known mechanical alignment (e.g., a fixture on the wall or table such as a surgical table) or by using the accelerometer/magnetometer approach as described above. Although gyroscopes may have a tendency to drift over an extended time, a gyroscopic approach may be combined with another spatial determining approach to provide a redundant incremental check on base orientations during use (e.g. during surgery in surgical examples). For example, accelerometer, magnetometer, and gyroscope measurements may be used together to determine relative orientations and transformations between base links. As another example, gyroscope measurements may be combined with other spatial determining methods to add robustness and redundancy, and to simplify or speed up estimations. In addition, gyroscopes may be used to detect transient disturbances in the magnetic field that cause a deflection of a bearing measurement that does not agree with the gyroscope data. In this aspect, gyroscope data is optionally more heavily weighted until the magnetometer signal stabilizes. Or, the detection of a transient magnetic field disturbance may be used to signal a problem or fault to the user. A single DOF adjustment to allow the user to fine tune the perceived alignment in a reduced parameter space as described above may be incorporated into implementations that incorporate gyroscopic information.

As another alternative spatial determining approach, only acceleration sensors are used, and vibration sensors (see e.g., FIG. 6, sensors 624a-624c including vibration sensing/injecting units) are used to determine relative spatial relationships between units. In one implementation, ambient common mode vibration (e.g., from the floor) is sensed at each patient side unit or cannula. Assuming the same ambient vibration is sensed by each unit, a common mode signal is identified by accelerometers associated with and fixed at known orientations to each unit. The gravity vector and sensed horizontal directions of the vibrations at each unit are used to determine relative orientation between units. In an alternative implementation, a common mode vibration is injected. For example, a cannula is vibrated so that its remote center of motion at the body wall vibrates in a known direction. The injected vibration directions are sensed by the units, and the relative spatial orientation is determined.

In yet another implementation that uses vibration information, one or more beacons are placed (e.g., on the operating room floor) to inject periodic and time-synchronized common mode vibrations so that each unit can sense the vibrations. Accelerometers or matched resonators on the units sense the vibration. Time of flight measurement is used to establish distance to the vibrating beacon or beacons, and triangulation is used to determine the relative spatial orientation of the units. For example, assuming speed of sound in concrete is 3500 m/s, a 1 cm resolution requires ~3 μs time resolution. This approach advantageously eliminates the need for a clear line-of-sight between beacon and sensor. In all approaches that incorporate vibration injection, vibration frequency may be selected outside the audible range.

In another implementation, orientation degrees of freedom are optionally measured by using two or more different approaches. For example, an accelerometer may be used to determine orientation in two axes and machine vision is used to determine a bearing orientation in the remaining axis. The determinations are fused, and the fused result provides the complete 3-axis solution.

Thus a spatial determining system is used to determine the relative orientations and required transformations between multiple teleoperated system units in order to establish and maintain the required user's intuitive perception of control alignment between hand-operated master control devices and corresponding tools. Advantageously, only orientation information is used to establish and maintain the alignments required for master/slave control, or orientation information combined with less than complete position information is used to establish and maintain the alignments required for master/slave control.

5. Further Implementations

Many implementations have been described in terms of a telesurgical system, but it should be understood that inventive aspects are not limited to telesurgical systems. Implementations in various other teleoperated systems are contemplated. For example, aspects may be implemented in teleoperated systems with military applications (e.g., bomb disposal, reconnaissance, operations under enemy fire), research applications (e.g., marine submersibles, earth-orbiting satellites and manned stations), material handling applications (e.g., nuclear "hot cell" or other hazardous materials), emergency response (e.g., search and rescue, firefighting, nuclear reactor investigation), unmanned ground vehicles (e.g., agricultural, manufacturing, mining, construction), and the like.

We claim:

1. A teleoperated system comprising:
 a first means for determining:
  an orientation of an end-effector reference frame relative to a field-of-view reference frame, the end-effector reference frame moveable relative to the field-of-view reference frame, the end-effector reference frame being defined for an end effector of a tool, and the field-of-view reference frame being defined for a field of view of an imaging device, and
  an orientation of an input-device reference frame relative to a display reference frame, the input-device reference frame being defined for a master input device, and the display reference frame being defined for a displayed image;
 a second means for establishing a first alignment relationship, the first alignment relationship comprising an end-effector-to-field-of-view alignment relationship or an input-device-to-display alignment relationship, wherein the end-effector-to-field-of-view alignment relationship is between the end-effector reference frame and the field-of-view reference frame and independent of a position relationship between the end-effector reference frame and the field-of-view reference frame, and wherein the input-device-to-display alignment relationship is between the input-device reference frame and the display reference frame and independent of a position relationship between the input-device reference frame and the display reference frame; and
 a third means for commanding, based on the first alignment relationship, a change in a pose of the end effector in response to a change in a pose of the master input device.

2. The teleoperated system of claim 1, wherein:
 the first alignment relationship comprises the end-effector-to-field-of-view alignment relationship;
 the second means is configured for establishing a second alignment relationship, the second alignment relationship comprising the input-device-to-display alignment relationship; and
 the third means is configured for commanding the change in the pose of the end effector further based on the second alignment relationship.

3. The teleoperated system of claim 2, wherein an orientation of the input-device reference frame relative to the display reference frame is a first relative orientation, wherein the orientation of the end-effector reference frame relative to the field-of-view reference frame is a second relative orientation, wherein the first relative orientation differs from the second relative orientation by a difference, and wherein the teleoperated system further comprises:
 a fourth means for updating the second alignment relationship multiple times to gradually reduce the difference.

4. The teleoperated system of claim 1,
 wherein the pose of the end effector is relative to the field-of-view reference frame;
 wherein the pose of the master input device is relative to the display reference frame; and
 wherein the change in the pose of the end effector includes: a change in an orientation of the end effector relative to the field-of-view reference frame corresponding to a change in an orientation of the master input device relative to the display reference frame.

5. The teleoperated system of claim 1, further comprising:
 a fourth means for establishing a teleoperated master-slave control relationship based on the first alignment relationship.

6. The teleoperated system of claim 1, wherein the first means is configured for:
 determining a complete position of at least one reference frame selected from the group consisting of: the field-of-view reference frame, the end-effector reference frame, the display reference frame, and the input-device reference frame; or determining a complete position of the end-effector reference frame relative to the field-of-view reference frame; or determining a complete position of the input-device reference frame relative to the display reference frame.

7. The teleoperated system of claim 1, wherein the first means is configured for:

determining less than a complete position of the end-effector reference frame relative to the field-of-view reference frame; or determining less than a complete position of the input-device reference frame relative to the display reference frame.

8. A teleoperated system comprising:

a first means for determining:

a complete orientation of a field-of-view reference frame defined for a field of view of an imaging device, a complete orientation of an end-effector reference frame defined for an end effector of a tool;

a complete orientation of a display reference frame defined for a display;

a complete orientation of a master-device reference frame defined for a master device;

a second means for establishing a teleoperated master/slave control relationship between a master device and the end effector by establishing a first alignment relationship, the first alignment relationship comprising an end-effector-to-field-of-view alignment relationship or a master-device-to-display alignment relationship, wherein the end-effector-to-field-of-view alignment relationship is between the end-effector reference frame and the field-of-view reference frame and is based on less than complete position information relating the end-effector reference frame and the field-of-view reference frame, wherein the master-device-to-display alignment relationship is between the master-device reference frame and the display reference frame, and wherein the first alignment relationship between the master-device reference frame and the display reference frame being is based on less than complete position information relating the master-device reference frame and the display reference frame; and a third means for executing the master/slave control relationship between the master device and the end effector by changing a pose of the end effector to correspond to a change in a pose of the master device.

9. The teleoperated system of claim 8, wherein the pose of the end effector is relative to the field-of-view reference frame;

wherein the pose of the master device is relative to the display reference frame; and wherein the change in the pose of the end effector includes: a change in an orientation of the end effector relative to the field-of-view reference frame corresponding to a change in an orientation of the master device relative to the display reference frame.

10. The teleoperated system of claim 8, wherein the first means is configured for:

determining partial position information of at least one reference frame selected from the group consisting of: the field-of-view reference frame, the end-effector reference frame, the display reference frame, and the master-device reference frame.

11. The teleoperated system of claim 8, wherein changing the pose of the end effector to correspond to the change in the pose of the master device comprises:

changing a direction of movement of the end effector to correspond to a change in direction of movement of the master device.

12. A teleoperated system comprising:

a first means for determining an orientation of an end-effector reference frame relative to a field-of-view reference frame, the end-effector reference frame being associated with an end effector of a tool, and the field-of-view reference frame being associated with a field of view of an imaging device, and an orientation of an input-device reference frame relative to an image-presentation reference frame, the input-device reference frame being associated with an input device, and the image-presentation reference frame being associated with an image presented to a user;

a second means for establishing a first alignment relationship, the first alignment relationship comprising an end-effector-to-field-of-view alignment relationship or an input-device-to-image-presentation alignment relationship;

wherein the end-effector-to-field-of-view alignment relationship is between the end-effector reference frame and the field-of-view reference frame and independent of a position relationship between the end-effector reference frame and the field-of-view reference frame, and wherein the input-device-to-image-presentation alignment relationship is between the input-device reference frame and the image-presentation reference frame and independent of a position relationship between the input-device reference frame and the image-presentation reference frame; and a third means for commanding, based on the first alignment relationship, a change in a pose of the end effector in response to a change in a pose of the input device.

13. The teleoperated system of claim 12, wherein:

the second means is configured for establishing a second alignment relationship, the second alignment relationship comprising the input-device-to-image-presentation alignment relationship; and the third means is configured for commanding the change in the pose of the end effector is further based on the second alignment relationship.

14. The teleoperated system of claim 13, wherein the orientation of the input-device reference frame relative to the image-presentation reference frame is a first relative orientation, wherein the orientation of the end-effector reference frame relative to the field-of-view reference frame is a second relative orientation, and wherein the first relative orientation differs from the second relative orientation by a difference, the teleoperated system further comprising:

a fourth means for updating the second alignment relationship multiple times to gradually reduce the difference.

15. The teleoperated system of claim 12, wherein the first alignment relationship comprises the input-device-to-image-presentation alignment relationship.

16. The teleoperated system of claim 12, wherein commanding the change in the pose of the end effector comprises:

commanding a change in an orientation of the end effector relative to the field-of-view reference frame to correspond to a change in an orientation of the input device relative to the image-presentation reference frame.

17. The teleoperated system of claim 12, further comprising:
- a fourth means for establishing a teleoperated master-slave control relationship based on the first alignment relationship.

18. The teleoperated system of claim 12,
- wherein determining the orientation of the end-effector reference frame relative to the field-of-view reference frame comprises:
  - determining a complete orientation of the field-of-view reference frame, and
  - determining a complete orientation of the end-effector reference frame; and
- wherein determining the orientation of the input-device reference frame relative to the image-presentation reference frame comprises:
  - determining a complete orientation of the image-presentation reference frame, and
  - determining a complete orientation of the input-device reference frame.

19. The teleoperated system of claim 12, wherein the first means is configured for:
- determining a complete position of at least one reference frame selected from the group consisting of: the field-of-view reference frame, the end-effector reference frame, the image-presentation reference frame, and the input-device reference frame; or
- determining a complete position of the end-effector reference frame relative to the field-of-view reference frame; or
- determining a complete position of the input-device reference frame relative to the image-presentation reference frame.

20. The teleoperated system of claim 12, wherein the first means is configured for:
- determining less than a complete position of the end-effector reference frame relative to the field-of-view reference frame; or
- determining less than a complete position of the input-device reference frame relative to the image-presentation reference frame.

* * * * *